United States Patent
Hahn et al.

(10) Patent No.: US 9,422,552 B2
(45) Date of Patent: Aug. 23, 2016

(54) MODIFIED SINA

(75) Inventors: Peter Hahn, Bergisch Gladbach (DE); Eric Lader, Boyds, MD (US); Wolfgang Bielke, Mechemich (DE); Alexander Azzawi, Solingen (DE); Jie Kang, Hann (DE)

(73) Assignee: QIAGEN GMBH, Hilden (GB)

( * ) Notice: Subject to any disclaimer, the term of this patent is extended or adjusted under 35 U.S.C. 154(b) by 16 days.

(21) Appl. No.: 13/378,601

(22) PCT Filed: Jun. 11, 2010

(86) PCT No.: PCT/EP2010/003501
§ 371 (c)(1),
(2), (4) Date: Feb. 23, 2012

(87) PCT Pub. No.: WO2010/145778
PCT Pub. Date: Dec. 23, 2010

(65) Prior Publication Data
US 2012/0142011 A1 Jun. 7, 2012

(30) Foreign Application Priority Data
Jun. 15, 2009 (EP) .................................... 09007835

(51) Int. Cl.
*C12N 15/11* (2006.01)
*C07H 21/04* (2006.01)
*C12N 15/113* (2010.01)

(52) U.S. Cl.
CPC ............ *C12N 15/111* (2013.01); *C12N 15/113* (2013.01); *C12N 2310/14* (2013.01); *C12N 2310/332* (2013.01); *C12N 2320/51* (2013.01)

(58) Field of Classification Search
CPC ........... C12N 15/113; C12N 2310/321; C12N 2310/14; C12N 2310/332; C12N 2310/11; C12N 2320/53; C12N 15/111; C12N 2310/314; A61K 31/713; C07H 21/00
See application file for complete search history.

(56) References Cited

U.S. PATENT DOCUMENTS

2005/0223427 A1* 10/2005 Leake et al. .................. 800/286
2005/0233342 A1* 10/2005 Manoharan et al. .............. 435/6
2006/0217332 A1* 9/2006 Vargeese et al. ................ 514/44

FOREIGN PATENT DOCUMENTS

WO WO 2009/044392 4/2009

OTHER PUBLICATIONS

O'Gara et al., Structures of HhaI methyltransferase complexed with substrates containing mismatches at the target base, 1998, Nature Structural Biology, vol. 5, pp. 872-877.*
Dash et al., Examining Ty3 polypurine tract structure and function by nucleoside analog interference, 2006, The Journal of Biological Chemistry, vol. 281, pp. 2773-2783.*
"dSpacer CE Phosphoramidite", Catalog number: 10-1914-xx, Glen Research, accessed and retrieved from www.glenresearch.com on Apr. 22, 2014.*
Zhang et al., 2001, Analytical Chemistry, vol. 73, pp. 3263-3273.*
Wang et al., C3-spacer-containing circular oligonucleotides as inhibitors of human topoisomerase I, 2008, Bioorganic & Medicinal Chemistry Letters, vol. 18, pp. 3597-3602.*
Safety data sheet, dSpacer CE phosphoramidite, Product code 10-1914-xx, Glen Research, Printing date Nov. 4, 2011.*
Safety data sheet, rSpacer CE phosphoramidite, Product code 10-3914-xx, Glen Research, Printing date Nov. 4, 2011.*
Behlke M.A.: "Chemical modification of siRNAs for in vivo use", Oligonucleotides, vol. 18, 2008, pp. 305-320.
Chen P.Y. et al.: "Strand-specific 5'-0-methlyation of siRNA duplexes controls guide strand selection and targeting specificity", RNA, vol. 14, 2008, pp. 263-274.
Snove O. Jr. and Rossi J.J.: "Chemical modifications rescue off-target effects of RNAI", ACS Chemical Biology, vol. 1, No. 5, Jun. 20, 2006, pp. 274-276.
Jackson A. L. et al.: "Position-specific chemical modification of siRNAs reduces "off-target" transcropt silencing", RNA, vol. 12, 2006, pp. 1197-1205.
Corey D. R.: "Chemical modification: the key to clinical application of RNA interference?", The Journal of Clinical Investigation, vol. 177, No. 12, Dec. 2007, pp. 3615-3622.
Watts J. K. et al: "Chemically modified siRNA: tools and applications", Drug Discovery Today, vol. 13, No. 19/20, Oct. 2008, pp. 842-855.

* cited by examiner

*Primary Examiner* — Dana Shin
(74) *Attorney, Agent, or Firm* — Fanelli Haag PLLC

(57) ABSTRACT

The present invention pertains to the use of at least one abasic modification within the first 8 nucleotide positions of the 5' region of the antisense strand of a small interfering nucleic acid (siNA) molecule for reducing off-target effects. Provided are suitable modified siNAs, compositions and methods for producing respective siNAs, as well as kits comprising respective siNAs.

9 Claims, 17 Drawing Sheets

Fig. 1

Figure 2:
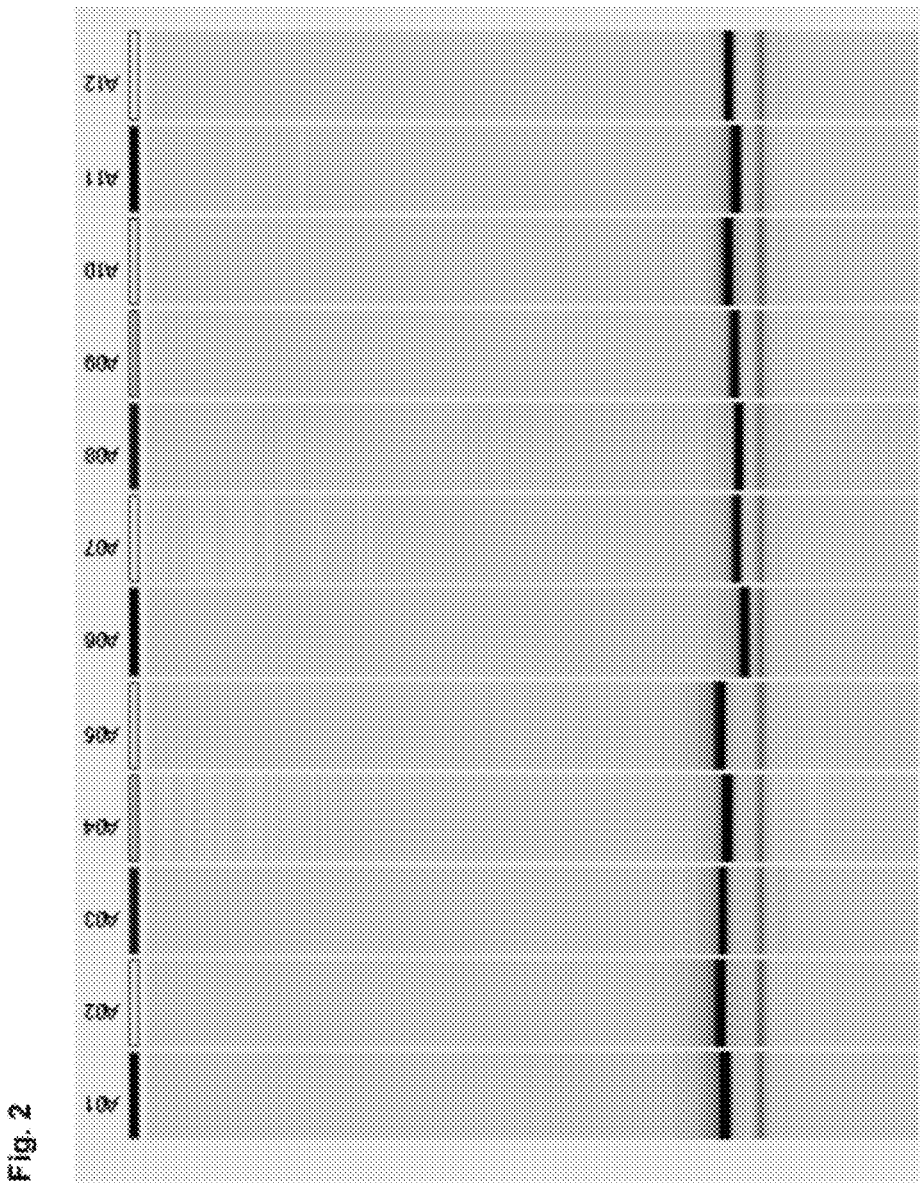

A
5'—N⁺N N N N N N N N N N N N N N N N N N N—3'
    | | | | | | | | | | | | | | | | | |
3'—N N N*N*N*N*N*N*N*N*N*N*N*N*N*N*N^N*^ N* —p —5'

B
5'—N⁺N N N N N N N N N N N N N N N N N N N—3'
    | | | | | | | | | | | | | | | | | |
3'—N N N*N*N*N*N*N*N*N*N*N*N*N*N*N*N*N*N^ N* —p —5'

C
5'—N⁺N N N N N N N N N N N N N N N N N N N—3'
    | | | | | | | | | | | | | | | | | |
3'—N N N*N*N*N*N*N*N*N*N*N*N*N*N*N*N*N*N^ N* —p —5'

N: nucleotide; N*: complementary nucleotide; N⁺: 5-OMe modified nucleotide; ^: abasic modification; p: 5'-phosphate

SEQUENCE LISTING

<160> NUMBER OF SEQ ID NOS: 14

<210> SEQ ID NO 1
<211> LENGTH: 21
<212> TYPE: DNA
<213> ORGANISM: Artificial
<220> FEATURE:

<223> OTHER INFORMATION: siRNA target sequence

<400> SEQUENCE: 1
aaggccaaga tccaagataa a                                              21

<210> SEQ ID NO 2
<211> LENGTH: 21
<212> TYPE: DNA
<213> ORGANISM: Artificial
<220> FEATURE:
<223> OTHER INFORMATION: siRNA target sequence

<400> SEQUENCE: 2
aagcgccaga atggagatga t                                              21

<210> SEQ ID NO 3
<211> LENGTH: 21
<212> TYPE: DNA
<213> ORGANISM: Artificial
<220> FEATURE:
<223> OTHER INFORMATION: siRNA target sequence

<400> SEQUENCE: 3
caagttcgac atggaattgg a                                              21

<210> SEQ ID NO 4
<211> LENGTH: 21
<212> TYPE: DNA
<213> ORGANISM: Artificial
<220> FEATURE:
<223> OTHER INFORMATION: siRNA target sequence

<400> SEQUENCE: 4
ttggatgact tgcctaagga a                                              21

<210> SEQ ID NO 5
<211> LENGTH: 21
<212> TYPE: DNA
<213> ORGANISM: Artificial
<220> FEATURE:
<223> OTHER INFORMATION: siRNA target sequence

<400> SEQUENCE: 5
aatgctgact ccaaagctct g                                              21

<210> SEQ ID NO 6
<211> LENGTH: 21
<212> TYPE: DNA
<213> ORGANISM: Artificial
<220> FEATURE:
<223> OTHER INFORMATION: siRNA target sequence

<400> SEQUENCE: 6
ttgactaact atggaagatt a                                              21

<210> SEQ ID NO 7
<211> LENGTH: 21
<212> TYPE: DNA
<213> ORGANISM: Artificial
<220> FEATURE:
<223> OTHER INFORMATION: siRNA target sequence

<400> SEQUENCE: 7
caggactata agaatacatt t                                              21

```
<210> SEQ ID NO 8
<211> LENGTH: 21
<212> TYPE: DNA
<213> ORGANISM: Artificial
<220> FEATURE:
<223> OTHER INFORMATION: siRNA target sequence

<400> SEQUENCE: 8
tcgggaaatt tctctattaa a                                              21

<210> SEQ ID NO 9
<211> LENGTH: 21
<212> TYPE: DNA
<213> ORGANISM: Artificial
<220> FEATURE:
<223> OTHER INFORMATION: siRNA target sequence

<400> SEQUENCE: 9
tggggtcagc tcgttactca a                                              21

<210> SEQ ID NO 10
<211> LENGTH: 21
<212> TYPE: DNA
<213> ORGANISM: Artificial
<220> FEATURE:
<223> OTHER INFORMATION: siRNA target sequence

<400> SEQUENCE: 10
aagagtgaca gttgaggcta a                                              21

<210> SEQ ID NO 11
<211> LENGTH: 21
<212> TYPE: DNA
<213> ORGANISM: Artificial
<220> FEATURE:
<223> OTHER INFORMATION: siRNA target sequence

<400> SEQUENCE: 11
aacaaagaat atgaaatatc t                                              21

<210> SEQ ID NO 12
<211> LENGTH: 21
<212> TYPE: DNA
<213> ORGANISM: Artificial
<220> FEATURE:
<223> OTHER INFORMATION: siRNA target sequence

<400> SEQUENCE: 12
ccagaaagag gctcaaatta a                                              21

<210> SEQ ID NO 13
<211> LENGTH: 21
<212> TYPE: DNA
<213> ORGANISM: Artificial
<220> FEATURE:
<223> OTHER INFORMATION: siRNA target sequence

<400> SEQUENCE: 13
tcagacagag actttatgga a                                              21

<210> SEQ ID NO 14
<211> LENGTH: 19
```

```
<212> TYPE: RNA
<213> ORGANISM: Artificial
<220> FEATURE:
<223> OTHER INFORMATION: siNA antisense strand

<400> SEQUENCE: 14
aggaguucca cauucuggc                                              19
```

US 9,422,552 B2

MODIFIED SINA

CROSS-REFERENCE TO RELATED APPLICATION

This application is a National Stage of PCT/EP2010/003501, filed Jun. 11, 2010 which claims priority to European Application No. 09007835.3, filed Jun. 15, 2009, the disclosures of which are incorporated herein by reference in their entirety.

FIELD OF THE INVENTION

The present invention pertains to modified short interfering nucleic acid (siNA) molecules capable of downregulating a target gene via RNA interference and showing reduced off-target effects. Also provided are methods for producing respective modified siNA molecules as well as uses and applications thereof, in particular in RNAi experiments.

The instant application contains a Sequence Listing which has been submitted in ASCII format is EFS-Web and is hereby incorporated by reference in its entirety. Said ASCII copy, created on Dec. 15, 2011, is named 0051_0052_US1 Sequence_Listing.txt and is 2768 bytes in size.

BACKGROUND OF THE INVENTION

RNA interference (RNAi) has become a widely used tool for functional genomic studies in vertebrate and invertebrates. RNAi works by silencing a gene through homologous short interfering dsRNAs (for example siRNAs), which trigger the destruction of the corresponding mRNA by the RNA-induced silencing complex (RISC). The selective and robust effect of RNAi on gene expression makes it a valuable research tool, both in cell culture and in living organisms. Synthetic dsRNA introduced into cells can induce suppression of specific genes of interest. The effect of these genes on the phenotype of the cells can then be analyzed by studying the effect of the gene silencing. RNAi may also be used for large-scale screens that systematically shut down each gene in the cell, which can help identify the components necessary for a particular cellular process or an event such as for example, cell division.

Due to its advantages, in particular siRNA-mediated RNAi has become an indispensable tool in functional genomic research. Chemically synthesized siRNA reagents that target every gene in a human, mouse and rat genome are available for convenient delivery in vitro. Data acquired from RNAi experiments are used to support important conclusions about how genes function. For the above reasons, the RNA interference pathway is often exploited in experimental biology to study the function of genes in cell culture and in vivo in model organisms. Double-stranded RNA is synthesized with a sequence complementary to the target sequence of a gene of interest, usually an 18 to 30 mer and introduced into the cell or organism, where it is recognized as exogenous genetic material and activates the RNAi pathway. Using this mechanism, researchers can cause a drastic decrease in the expression of the targeted gene. Studying the effects of this decrease can show the physiological role of the respective targeted gene product. Since RNAi may not necessarily totally abolish expression of the gene, this technique is sometimes referred to as a "knockdown" to distinguish it from "knockout" procedures, in which expression of a gene is entirely eliminated, e.g. by introducing a knock-out mutation in the target gene and thus the DNA. The ease, speed, and cost-effectiveness have made RNAi the method of choice in particular for loss-of-gene function studies.

However, even though RNAi is a valuable tool for several applications in research as well as in therapeutic applications it has produced a new set of problems regarding the specificity of the RNAi mediating molecule. It was shown that unspecific off-target effects of the transfected/provided RNAi mediating compounds may constitute a major problem. This, as the off-target effects may overlay the specific effect of the transfected RNAi mediating compound (e.g. siRNA). Many off-target effects of transfected RNAi inducing compounds such as siRNA occur because the siRNA may act like a miRNA, by binding to partially homologue sequences in the 3' UTR region of the mRNAs. This binding may lead to an unwanted regulation of mRNA targets, which are not supposed to be targeted/regulated by the particular RNAi mediating compound.

Although it is possible to achieve single base discrimination with selected siNAs, single—or even double—base mismatches are often tolerated and can still reduce target levels by significant amounts. If the full sequence of the reference genome is known, a thorough homology screen of candidate siNAs might permit exclusion of sites where unwanted homology exists with other genes and theoretically lead to high specificity. Unfortunately, this kind of traditional cross-hybridization analysis can be less effective than expected and even carefully screened siNAs can cause significant changes in the expression level of unrelated genes. As it is outlined above, it appears that many of these effects are mediated by the unintended participation of siNAs in miRNA pathways.

The miRNA translational suppression pathway is often directed by imperfect base pairing between the target and antisense strand and the specificity of this process is defined by 6 to 8 base "seed region" at the 5' end of the antisense strand of the miRNA. Given the expected frequency of finding 6 to 7 base matches between a siNA and a non target gene within the entire transcriptome, it is not surprising that off-target effects mediated by this mechanism can simultaneously affect hundreds of genes. Target sites for miRNA binding seem to be enriched in the 3'-untranslated region (3'UTR) of genes and a careful focus on homology screening of the seed regions of candidate siRNAs in the 3'UTR of all genes may be prudent. Unfortunately, 6-base matches are very common, and only a few of these matches actually proved to be real functional sites that can lead to target gene suppression.

Therefore, means for reducing in particular miRNA pathway derived off-target effects is needed beyond seed region homology screening and proper controls and comparative experiments in order to obtain reliable RNAi based results in order to enhance the specificity e.g. for research or therapeutic applications of the siNA.

Although siNAs such as in particular siRNAs have two strands, only functional participation of the guide strand (also referred to as the antisense strand) is desired. Design of the siNA can introduce strand bias into the siNA so that one strand is preferentially incorporated into RISC. However, this bias is only relative and some variable amount of the passenger strand (also referred to as the sense strand) will be functionally loaded and can be engaged in undesired gene knockdown events. Various strategies has been developed in the prior art to reduce or totally eliminate participation of the sense strand of the siNA in gene silencing. One approach is to cleave the sense strand so that the RNA duplex is comprised of an intact antisense strand which is annealed to two adjoining shorter sense strand RNA oligomers. This design has been called "small internally segmented siRNA". Another approach is to use modifications that block the 5' end of the sense strand of the siNA. Both strands of the endogenous siRNAs or miRNAs naturally have a 5'-phosphate (which results from Dicer cleavage). Synthetic siNAs are usually made with a 5'-phosphate or 5'-hydroxyl (in which case the siRNAs phosphorylated by the cellular RNA kinase hClp1). Although synthetic siNAs are tolerant of some 5'-modifications, blocking the 5'end of a siNA strand (by, for example, 5'-O-methylation) can reduce or eliminate participation of that strand in silencing.

The use of site-specific chemical modification may also permit reduction or elimination of off-target effects derived from unwanted participation of the antisense strand in miRNA pathways. Several groups have studied chemical modification patterns looking for selective modification strategies that retain potency of the siNA antisense strand to direct Ago2 cleavage of an mRNA target while reducing participation of that siNA in miRNA-like seed-region directed events. For example placing a single 2'OMe residue at position +2 of the guide strand can substantially reduce seed region-related off-target effects. Furthermore, replacing the entire seed region with DNA residues maintained functional potency for knockdown of the intended target while reducing seed region-related off-target effects.

Thus, the use of chemical modifications in the siNA molecules may reduce off-target effects that arise either from triggering the innate immune system as well as reduce the ability of a siNA to participate in seed-region directed miRNA-pathway off-target effects.

It is the object of the present invention to provide a siNA molecule which is capable of efficiently down regulating a target gene via RNA interference which shows reduced off-target effects, in particular compared to unmodified molecules. In particular, the unwanted participation of the antisense strand in miRNA pathways is to be reduced.

SUMMARY OF THE INVENTION

The present invention pertains to novel modified siNA molecules showing reduced off-target effects.

According to a first aspect, an at least partially double stranded short interfering nucleic acid (siNA) molecule capable of downregulating a target gene via RNA interference is provided, comprising a sense strand and an antisense strand, wherein the antisense strand has sufficient complementarity to the target sequence to mediate RNA interference and wherein said antisense strand comprises at least one abasic modification within the first 8 nucleotide positions of the 5' region.

It has been found that the incorporation of an abasic modification in the seed region of the antisense strand of the siNA molecule considerably reduces off-target effects.

The present invention also pertains to the use of at least one abasic modification within the first 8 nucleotide positions of the 5' region of the antisense strand of a siNA molecule to reduce off-target effects.

According to a further aspect of the present invention a composition comprising a siRNA molecule according to the present invention is provided. Furthermore, a method for producing a siNA molecule according to the present invention is provided as well as a method for performing an RNAi experiment using the modified siNA according to the present invention. Also provided is a kit, comprising the modified siNA according to the present invention, which shows reduced off-target effects.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present invention provides an at least partially double stranded short interfering nucleic acid (siNA) molecule capable of downregulating a target gene via RNA interference, which comprises a sense strand and an antisense strand, wherein the antisense strand has sufficient complementarity to the target sequence to mediate RNA interference and wherein said antisense strand comprises at least one abasic modification within the first 8 nucleotide positions of the 5' region.

The basic idea of the present invention is to provide a siNA molecule which comprises an abasic modification in the seed region of the antisense strand. The numbering/counting of the nucleotide positions starts with nucleotide +1 from the 5'end of the region substantially complementary to the target sequence in the gene to be silenced for each strand. It is believed that the abasic modification that is incorporated in the 5'region of the antisense strand reduces the binding strength of the antisense strand in the respective region when it anneals to an at least partially complementary sequence. It was surprisingly shown, that thereby off-target effects can be efficiently reduced and the specificity of the siNA molecule for the target sequence/gene is increased.

Without being bound by theory, it is believed that many off-target effects are caused by the antisense strand which accidentally silences non-target genes in a miRNA like fashion (see above). For a respective miRNA related off-target regulation, usually only the first 1 to 7 or 1 to 8 nucleotides of the 5'end of the antisense strand (which is also referred to as the seed region) are involved in binding and thus are responsible for the off-target effects. As only a few nucleotides contribute to this seed-induced non-target binding, an abasic modification in this seed region of the antisense strand has a very strong influence on the binding and therefore on the inducement of off-target effects. As due to the abasic modification in the seed region a base is missing that would otherwise contribute to binding of the seed region via Watson/Crick pairing, off-target effects are efficiently reduced as the seed region can not bind sufficiently strong with the remaining bases of the seed region of the antisense strand to a non-target sequence in order to induce the unwanted silencing. Basically, the seed binding capacity of the antisense strand is reduced due to the abasic modification in the 5'region of the antisense strand.

Regarding the target sequence that is to be downregulated by the siNA molecule according to the present invention, the abasic modification in the seed region of the antisense strand has a less strong influence, as usually the complete antisense strand—and thus more than the seed region—is involved in binding of the target sequence. Therefore, the introduction of the abasic modification at the 5'end of the antisense strand does not significantly reduce respectively disturb binding of the target sequence. Furthermore, as off-target effects are efficiently reduced due to the design of the siNA molecule, it is also possible to increase the concentration of the siNA molecule in an RNAi experiment in order to achieve the desired knock-down of the target gene of interest. Therefore, in case the potency of the siNA molecule should be reduced due to the incorporation of the abasic modification, this may be compensated by an increase of the used concentration.

Therefore, a novel modified siNA molecule is provided according to the teachings of the present invention, which is still capable of efficiently down-regulating the expression of the target gene but which reduces off-target effects by the introduction of an abasic modification at the 5'end region of the antisense strand.

The term "an abasic modification" in particular refers to a moiety that can replace a nucleotide and/or nucleoside in the antisense strand. Said abasic modification lacks a base suitable for Watson and Crick base pairing. Therefore, an abasic modification may comprise a chemical group in place of a base or no base at all. Abasic modifications include abasic modifications which are sugar moieties as well as chemical analoga which can be incorporated into a polynucleotide chain instead of a nucleotide. Suitable examples of abasic modifications are described in detail below and in particular refer to abasic DNA analoga (dSpacer), abasic RNA analoga (rSpacer) and abasic chemical analoga (cSpacer).

The terms "a short interfering nucleic acid" and "siNA" in particular refer to any nucleic acid molecule or functional variant or derivative thereof capable of mediating RNA interference (RNAi). The siNA molecule can be single or at least partially double stranded. The nucleic acid molecule or functional variant or derivative thereof may comprise modified nucleotides and may comprise RNA as well as DNA nucleotides and chemical analoga thereof. For example the siNA can be a double-stranded polynucleotide molecule comprising self-complementary sense and antisense strands. The siNA can be assembled from two separate polynucleotides, wherein one strand is the sense strand and the other is the antisense strand, wherein the antisense and sense strands are self-complementary (i.e. each strand comprises a nucleotide sequence/stretch that is complementary to the nucleotide sequence in the other strand). Also encompassed are precursors of respective double-stranded molecules that render respective double stranded molecules comprising a separate sense and a separate antisense strand upon processing. The siNA may also be assembled from a single polynucleotide, where the self-complementary sense and antisense regions of the siNA are linked e.g. by means of a nucleic acid based or non-nucleic acid-based linker(s). Herein, we refer to the sense and antisense regions of a single polynucleotide also as sense and antisense strand. Thus, the terms "sense strand" and "sense region" are synonyms as well as are "antisense strand" and "antisense region". The siNA can be a polynucleotide with a hairpin secondary structure, having self-complementary sense and antisense strands respectively regions. As used herein, siNA molecules are not limited to those molecules containing only RNA, but further encompasses chemically-modified nucleotides and non-nucleotides. As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, and others.

In order to efficiently induce silencing, the siNA is substantially complementary to the target sequence in order to downregulate the expression of the target gene by RNA interference. Suitable siNAs targeting the chosen/identified target sequences of the target genes on the RNA level can be identified by using proper computational methods, applying certain design-algorithms. Several methods are known and can be used in conjunction with the present invention in order to provide suitable siNAs.

Preferably, the siNA is a siRNA. As siRNA, the siNA is a double-stranded molecule preferably having 3' overhangs on each strand. Said siRNA compound may comprise desoxy— as well as ribonucleotides and furthermore, modified nucleotides. Several embodiments and variations of siRNA compounds are known in the prior art and can be used in conjunction with the present invention. The length of the sense strand and the antisense strand of said siRNA is usually between 18 and 35 nt, preferably between 19 and 27 nt. In particular, the sense stand and the antisense strand are independently for each other 20, 21, 22 or 23 nt long. The 3' overhangs on each end if present are preferably 2 nts long, but blunt ended molecules may also be used. Furthermore, additionally a 5' overhang may be present on the sense and/or the antisense strand, preferably being 1 or 2 nts long. "Overhang" in this respect means a stretch of one or more nucleotides at the 3' or 5' end of a strand that does not basepair with a nucleotide of the other strand. The other strand may or may not have (a) nucleotide(s) opposite to the overhang nucleotide(s). According to one embodiment, the 5' overhang is 1 nt long and is present in the sense strand.

As it is outlined above, the abasic modification according to the present invention is located in the seed region of the antisense strand. Therefore, the abasic modification is preferably located within the first 8, 7, 6 or preferably first 5 nucleotide positions of the 5'region of the antisense strand, even more preferably in the first 4, 3 or 2 nucleotide positions of the 5'region of the antisense strand. More preferably, the abasic modification is located within the region of nucleotides 2 to 8, nucleotides 2 to 7, nucleotides 2 to 6 or, in particular nucleotides 2 to 5, nucleotides 2 to 4 or nucleotides 2 and 3 of the antisense stand. Examples have shown that particularly good results are obtained when the abasic modification is located in position 2 of the antisense strand. In this respect, position 1 of the antisense strand is the nucleotide at the 5' end of the sequence which is substantially complementary to the target sequence in the gene to be silenced. Preferably, the antisense strand of the siNA according to the present invention does not comprise an abasic modification at position 1.

The siNA according to the present invention may comprise one or more abasic modifications in the above-mentioned region of the antisense strand. However, preferably only 1, 2, 3 or 4 abasic modifications are present, more preferably only 1 or 2, and most preferably the siNA according to the invention comprises only one abasic modification in the first 2, 3, 4, 5, 6, 7, or 8 nucleotides of the 5'region of the antisense strand. In preferred embodiments, the siNA according to the invention comprises only 2, more preferably only 1, and most preferably no further abasic modifications in the antisense strand.

According to one embodiment, the first nucleotide of the antisense strand is a part of the double stranded region that is formed with the sense strand. The abasic modification is preferably located within said double stranded region, thereby disrupting the Watson and Crick pairing and accordingly the double stranded region in the respective position. Despite this interruption due to the abasic modification we refer to said stretch/region as double stranded region and also count the position of the abasic modification to the double stranded region.

The antisense strand of the siNA molecule may or may not carry a phosphor residue at the 5'end. An antisense strand which does not carry a phosphor residue at the 5'end but for example a hydroxy group is usually phosphorylated within the cell (see above). However, in order to ensure efficient phosphorylation of the 5' end of the antisense strand, it is preferred that the antisense strand is phosphorylated at the 5'end during synthesis. This can be achieved during the chemical synthesis process of the siNA molecule, which is also described in further detail below. In case the siNA according to the invention carries further nucleotides attached to the 5' end of the antisense strand, for example the siNA is a short hairpin siNA (shNA) wherein the 5' end of the antisense strand is connected to the 3' end of the sense strand, the phosphate at the 5' end of the antisense strand is generated during the processing of the shRNA in the cell.

Furthermore, it was shown that it is also beneficial to modify the sense strand in order to reduce off-target effects that are attributable to binding of the sense strand to non-target sequences. Therefore, according to a preferred embodiment the sense strand comprises at least one modification in its 5'region that blocks the phosphorylation of the 5'end of the sense strand. A suitable modification for this purpose is the incorporation of a nucleotide with a 5'-OMe modification at the 5' end of the sense strand. Furthermore, any other modification which blocks phosphorylation of the 5' end of the nucleotide may be used. Examples of suitable modifications are 5' desoxynucleotides, 5'-O-R modifications wherein R is a straight chain, branched or cyclic alkyl group or an aryl group which preferably have from 1 to 20 carbon atoms and which may be substituted by one or more substituents selected from alkyl groups, aryl groups, halogen atoms, hydroxy, alkoxy, and optionally substituted amino groups. Particularly preferred are 5'-methoxy, 5'-ethoxy, 5'-n-propoxy, 5'-isopropoxy, 5'-butoxy and 5'-pentoxy modifications.

Several variants are feasible for incorporating a respective 5' modification in the sense strand. According to one embodiment, the sense strand comprises a 5' modified nucleoside which forms part of the double stranded region between the sense strand and the antisense strand. In this embodiment, the 5' modified nucleoside has a corresponding binding partner in the antisense strand. According to a different embodiment, the nucleoside comprising the 5' modification does not form part of the double stranded region between the sense and the antisense strand. In this embodiment, the respectively modified nucleoside of the sense strand does not have a corresponding binding partner in the antisense strand and thus forms part of a 5'overhang. Therefore, the 5' modification also works when it is not base-paired with the antisense strand. The 5' modification can be depending on the desired design of the sense strand selected from the group consisting of 5'-modified thymidine, 5'-modified adenosine, 5'-modified cytidine, 5'-modified guanosine and 5'-modified uridine, in particular 5'OMe-T, 5'OMe-A, 5'OMe-C, 5'OMe-G and 5'OMe-U. Preferably, the 5' modification is a 5' modified thymidine, most preferred 5'OMe-T. A respectively modified nucleoside can be added irrespective of the sequence of the antisense strand to the sense strand and therefore may have or may not have a corresponding binding partner in the antisense strand. Therefore, it is possible to introduce a 5' modification into the sense strand irrespective of the sequence of the antisense strand. The respective design/synthesis of the siRNA molecule is convenient and can be performed as a standard. According to one embodiment, 5' OMe-T is added which inactivates the sense strand according to the experimental results. As the sense strand does not participate in binding to the target sequence, the additional potentially non-matching 5' OMe-T does not reduce the specificity of the siNA to the target sequence.

Also in case the siNA is synthesised as one hairpin molecule, a respective 5' modification is possible on the future sense strand (the sense region). As is also shown in the figures, the hairpin molecule which is a precursor of the final siNA can also carry the abasic modification. Intracellular cleavage of the hairpin structure results in a 5' phosphate. The 3' overhang of the antisense strand can be varied in length as well as the loop size.

Preferably, the siNA according to the present invention forms a duplex and therefore a helix. Therefore, the modifications are preferably chosen such that the formation of the respective duplex, respectively helix, is not disturbed. The design is chosen such that the siNA is recognized by the RISC complex and capable of efficiently inducing RNAi.

According to one embodiment, the double stranded region between the sense and the antisense strand spans at least 19 nucleotide positions. As is outlined above, the abasic modification can be located within this stretch of 19 nucleotide positions. Of course, where the respective abasic modification is present, no Watson and Crick pairing can be formed between the sense and the antisense strand and the double stranded region is at this position interrupted. Still, we refer to a respective stretch as a double stranded region. The double stranded region may also comprise more nucleotide positions, for example at least 20, 22, 23 or at least 25 positions.

According to one embodiment the siNA molecule comprises a 3' overhang in the sense strand and/or the antisense strand. The respective overhang may comprise 2 or even 3 residues. Preferably the antisense strand comprises a sequence specific 3' overhang. The sense strand may comprise a sequence unspecific 3' overhang. As the sense strand does not participate in target binding the sequence unspecific overhang does not negatively influence the target specificity.

Of course, it is also within the scope of the present invention that the modified siNA molecule comprises further modified nucleotides. Examples thereof are described, for example, in Manoharan, M. (2004) Curr. Opin. Chem. Biol. 8(6), 570-579 and in WO 2006/102970. The entire content of these documents is incorporated herein by reference.

The abasic modification that is used in the seed region of the antisense strand may be selected from the group consisting of abasic DNA analoga (herein also referred to as dSpacer), abasic RNA analoga (herein also referred to as rSpacer) and abasic chemical analoga (herein also referred to as cSpacer). Abasic DNA nucleoside analoga are preferably 1',2', didesoxyribose molecules without a base at the C1 atom. A preferred example of an abasic RNA analoga is a 1'desoxyribose without a base at the C1 atom. As is outlined above, instead of a base also a different chemical moiety can be bound to the C1 atom of the dSpacer or the rSpacer which, however, is not capable of forming hydrogen bounds with the corresponding base of the sense strand and/or a base of a transcript.

In one embodiment, the abasic modification is a compound having Formula I or II:

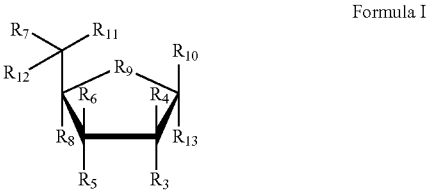

Formula I

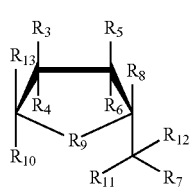

Formula II wherein each $R_3$, $R_4$, $R_5$, $R_6$, $R_7$, $R_8$, $R_{10}$, $R_{11}$, $R_{12}$, and $R_{13}$ is independently H, OH, alkyl, substituted alkyl, alkaryl or aralkyl, F, Cl, Br, CN, $CF_3$, $OCF_3$, OCN, $OPO_3H_2$, O-alkyl, S-alkyl, N-alkyl, O-alkenyl, S-alkenyl, N-alkenyl, SO-alkyl, alkyl-SH, alkyl-OH, O-alkyl-OH, O-alkyl-SH, S-alkyl-OH, S-alkyl-SH, alkyl-S-alkyl, alkyl-O-alkyl, $ONO_2$, $NO_2$, $N_3$, $NH_2$, aminoalkyl, aminoacid, aminoacyl, $ONH_2$, O-aminoalkyl, O-aminoacid, O-aminoacyl, heterocycloalkyl, heterocycloalkaryl, aminoalkylamino, polyalkylamino, or substituted silyl; $R_9$ is O, S, $CH_2$, S=O, CHF, or $CF_2$.

Preferred examples of abasic chemical analoga (cSpacer) that can be used as a abasic modification do not have a sugar backbone but are still capable of linking two ribose rings respectively desoxyribose rings of the antisense strand.

Several different abasic chemical analoga may be used. It is decisive that the formation of the duplex is not disturbed by the abasic chemical analoga and accordingly, that a siNA molecule is formed that is still recognized and processed by RISC. However, for this purpose, several abasic chemical analoga may be used. 1,3-propandiols and derivatives thereof are particularly suitable.

In one embodiment, the chemical abasic modification is a compound having Formula III:

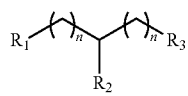

wherein each n is independently an integer from 0 to 12, each $R_1$, $R_2$ and $R_3$ is independently H, OH, alkyl, substituted alkyl, alkaryl or aralkyl, F, Cl, Br, CN, $CF_3$, $OCF_3$, OCN, $OPO_3H_2$, O-alkyl, S-alkyl, N-alkyl, O-alkenyl, S-alkenyl, N-alkenyl, SO-alkyl, alkyl-SH, alkyl-OH, O-alkyl-OH, O-alkyl-SH, S-alkyl-OH, S-alkyl-SH, alkyl-S-alkyl, alkyl-O-alkyl, $ONO_2$, $NO_2$, $N_3$, $NH_2$, aminoalkyl, aminoacid, aminoacyl, $ONH_2$, O-aminoalkyl, O-aminoacid, O-aminoacyl, heterocycloalkyl, heterocycloalkaryl, aminoalkylamino, polyalkylamino, or substituted silyl, and $R_1$, and $R_3$ serve as points of attachment to the neighbouring nucleotides of the siNA molecule of the invention. In a preferred embodiment, n is independently 0 or 1, in particular 1, $R_1$ forms a phosphodiester linkage to the C5 position of the 3'-adjacent nucleotide, $R_3$ forms a phosphodiester linkage to the C3 position of the 5'-adjacent nucleotide, and $R_2$ is hydrogen or hydroxy, preferably hydrogen.

Preferred examples of analoga are described by the following formulae which can be used to synthesise the siNA molecule according to the present invention. The abasic modification can be accordingly derived therefrom.

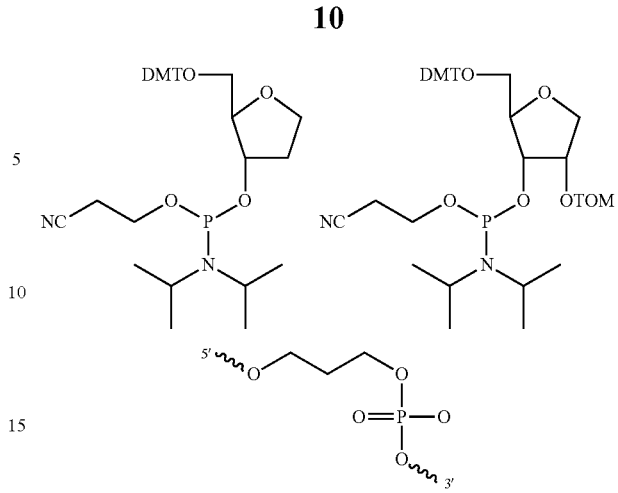

A preferred siNA according to the present invention comprises several of the above characteristics, namely
a) An abasic modification in position 2 of the antisense strand. As it is outlined above, the antisense strand preferably comprises an abasic modification in position 2 (the positions are numbered starting from the 5'end). It was shown that the incorporation of an abasic modification in position 2 has the strongest effect on the specificity of the antisense molecule. Therefore, off-target effects are particularly avoided when incorporating an abasic modification in position 2.
b) A 5'OMe modification at the 5'end of the sense strand. As is discussed above, a respective modification inactivates the sense strand, thereby avoiding off-target effects attributable to the sense strand.
c) A double stranded region between the sense and the antisense strand spanning at least 17, preferably at least 19 nucleotide positions wherein the abasic modification is located within said double-stranded region at position 2 of the antisense strand.

Preferably, the antisense strand is furthermore phosphorylated at the 5'end. The abasic modification is preferably a rSpacer or a C3 Spacer and thus a 1,3-propandiol. Experiments have shown that particularly good results are achieved with a respective combination of modifications.

In certain embodiments, the siNA of the present invention does not comprise a sense and antisense strand pair comprising the following modifications:
a sense strand comprising at least one unconventional moiety selected from the group consisting of an abasic ribose moiety, an abasic deoxyribose moiety, a deoxyribonucleotide, a modified deoxyribonucleotide, a mirror nucleotide, a non-base pairing nucleotide analog, a nucleotide joined to an adjacent nucleotide by a 2'-5' internucleotide phosphate bond bridged nucleic acids including LNA and ethylene bridged nucleic acids; and
an antisense strand comprising an abasic moiety in one of positions 5, 6, 7 or 8.

In certain embodiments, the antisense strand of the siNA of the present invention does not have any of the following modification patterns:
(i) 2'-O-methylated ribonucleotides at positions 2, 4, 6, 8, 11, 13, 15, 17 and 19 and an abasic modification at position 5;
(ii) 2'-O-methylated ribonucleotides at positions 2, 4, 8, 11, 13, 15, 17 and 19 and an abasic modification at position 6;
(iii) 2'-O-methylated ribonucleotides at positions 1, 2, 3, 7, 9, 11, 13, 15, 17 and 19 and an abasic modification at position 5;

(iv) 2'-O-methylated ribonucleotides at positions 1, 2, 3, 5, 7, 9, 11, 13, 15, 17 and 19 and an abasic modification at position 6;
(v) 2'-O-methylated ribonucleotides at positions 2, 4, 6, 7, 9, 11, 13, 15, 17 and 19 and an abasic modification at position 5;
(vi) 2'-O-methylated ribonucleotides at positions 1, 2, 4, 6, 7, 9, 11, 13, 15, 17 and 19 and an abasic modification at position 5;
(vii) 2'-O-methylated ribonucleotides at positions 2, 4, 6, 8, 11, 13, 15, 17 and 19 and an abasic modification at position 7; and
(viii) 2'-O-methylated ribonucleotides at positions 2, 4, 6, 11, 13, 15, 17 and 19 and an abasic modification at position 8.

In further embodiments, the antisense strand of the siNA of the present invention does not comprise the following nucleotide sequence:

```
                                        (SEQ ID NO: 14)
5'-AGG AGU UCC ACA UUC UGG C
``` wherein position 5, 6, 7 or 8 comprises an abasic modification.

Furthermore the present invention pertains to the use of at least one abasic modification, preferably an basic nucleoside and/or an abasic nucleoside analogon within the first 8 nucleotide position of the 5'region of the antisense strand of a siNA molecule to reduce off-target effects and in particular off-target effects attributable to the miRNA pathway. As it is outlined above, the inventors have found that the incorporation of an abasic modification into the seed region of the antisense strand considerably reduces off-target effects. This advantageous effect was not described previously in the prior art. Therefore, the present invention provides a valuable tool to avoid off-target effects in RNAi experiments. Preferred characteristics of the siNA molecule according to the present invention are described above. In particular, preferred examples of abasic modifications, positions for respective abasic modifications and further modifications of the sense and/or antisense strand are described above. They are particularly suitable to further improve this specificity and the performance of the siNA molecule according to the present invention. We refer to the above disclosure.

Also provided with the present invention is a composition comprising a siNA molecule according to the present invention. The characteristics of said siNA and preferred embodiments are described in detail above. We refer to the above disclosure.

Furthermore, a method of producing a siNA molecule according to the present invention is provided. Preferably, the siNA molecule is synthetically produced. For example, phosphoramidite chemistry as known in the art may be used for siNA synthesis. In particular, 2'-O-TOM-protected ribonucleoside phosphoramidites as described by Pitsch, S. et al. (2001) Helv. Chim. Acta 84, 3773-3795 may be used. Furthermore, the siNA may be synthesised using a solid support material.

Also provided is a method for performing an RNAi experiment, wherein a siNA according to the present invention is used for silencing a target gene. As it is outlined above, the siNA according to the present invention is more specific for the target of interest and thus shows considerably reduced off-target effects and is therefore particularly suitable for performing reliable RNAi experiments.

Also provided is a kit comprising a respectively modified siNA. The kit may optionally comprise buffers and reagents for performing the RNAi experiments.

The full contents of the text and documents as mentioned herein are incorporated herein by reference and form part of the present disclosure.

The following figures and examples serve the purpose to illustrate examples of the present invention without in any way limiting this scope thereof. However, they relate to preferred embodiments of the present invention.

FIGURES

FIG. 1 shows three examples of siNA molecules according to the present invention.

In FIG. 1a) the sense strand comprises a 5'-OMe modified nucleotide in position 1. The respective modified nucleotide is sequence specific, i. e. it pairs with the corresponding base of the antisense strand. Therefore, the antisense strand has a two base 3'overhang. The antisense strand is phosphorylated at the 5'end. The sense and the antisense strand pair with each other and thus form a double stranded region spanning 19 nucleotide positions. The antisense strand comprises an abasic modification in position 2 of the antisense strand which accordingly is located within the double stranded region. As is illustrated, no base pairing occurs at the position the abasic modification is located at. As is outlined in the description, the respective combination of modifications considerably increases the specificity of the siNA by reducing off-target effects of the sense as well as the antisense strand.

FIG. 1.b) shows an embodiment wherein the antisense strand comprises basically the same modifications as described in FIG. 1a). Please refer to our above discussion. The sense strand comprises a 5'-OMe modification as first nucleotide at the 5'end. The respective 5'-OMe modification has been introduced target-unspecifically. Thus, it was not considered whether the antisense strand comprises a base at the corresponding position that can pair with the 5'-OMe nucleotide. Therefore, the sense strand comprises one additional nucleotide and hence has a length of 22 nt while the antisense strand is only 21 nt long. Depending on the corresponding base of antisense strand the 5'-OMe nucleotide will in some cases pair with the opposing base and in some cases it won't. However, it was shown, that a respective one nucleotide overhang at the 5'end of the sense strand to introduce a 5'OMe modification does not disturb the function of the siNA. Therefore, the sequence unspecific incorporation of the respective modified nucleotide at the 5' end of the sense strand is a convenient way to block the phosphorylation of the 5'end of the sense strand and to reduce off-target effects that are mediated by the sense strand. This embodiment is also possible with a 21 nt sense strand. This would result in a 3 nt overhang in case no base pairing occurs.

In FIG. 1c) a similar scenario as in FIG. b) is shown. The antisense strand carries the same modifications as the embodiments shown in FIG. 1a) and FIG. 1b). In the shown embodiment, again a 5'-OMe modification has been added at the 5'end of the sense strand. Therefore, again a target unspecific modification has been introduced at position −1. Therefore, the sense strand comprises one additional nucleotide and hence has a length of 22 nt while the antisense strand is only 21 nt long. In this case, however, base pairing with the 2 nt overhang of the antisense strand occurs (as is the case statistically in 25%), thereby resulting in a 1 nt overhang at the antisense strand.

FIG. 2 Capillary gel electrophoresis for analysis of the individual siRNA duplexes.

Figure 3:
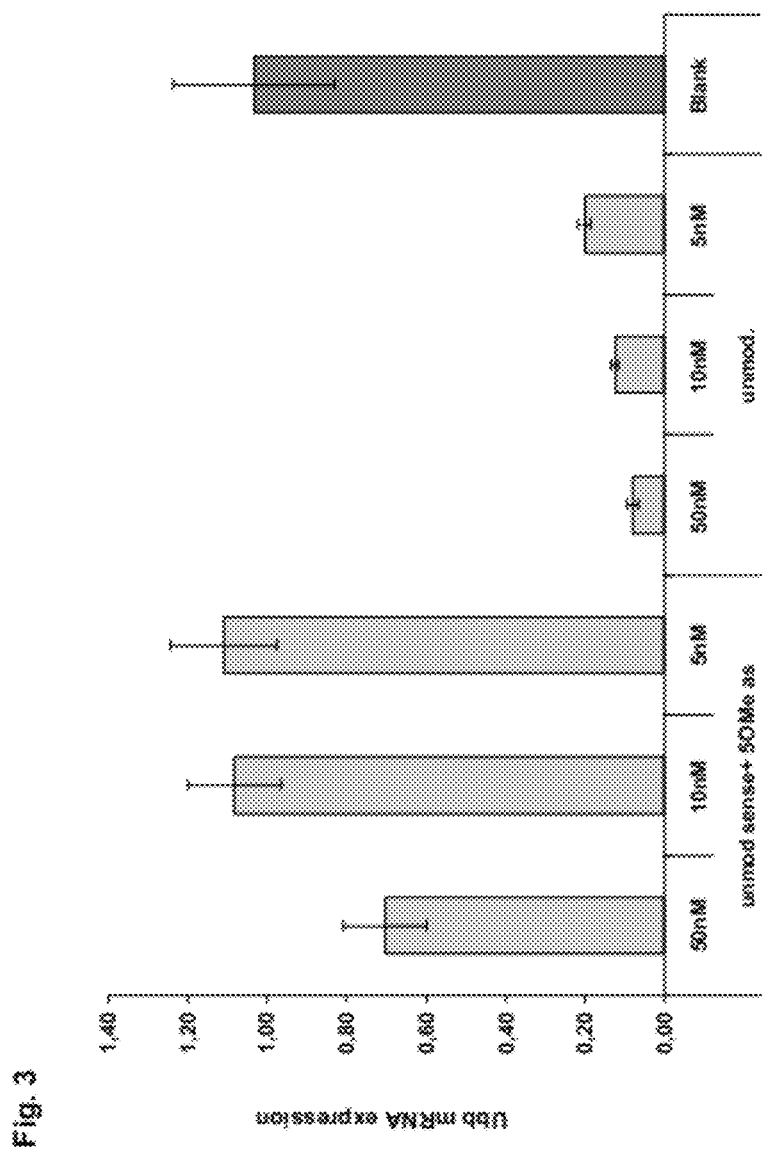

FIG. 3 HeLa S3 cells transfected with Ubiquitin b (Ubb)-specific siRNA: The unmodified duplex is compared with a 5'-OMe modified antisense strand (21-mer, no 5'-mismatch). The 5'-OMe nucleotide is part of the complementary region of the antisense strand. Analysis is performed 48 h after transfection by qRT PCR. Blank=no siRNA was transfected. The results show that the 5' OMe modified strand is not functional.

Figure 4:
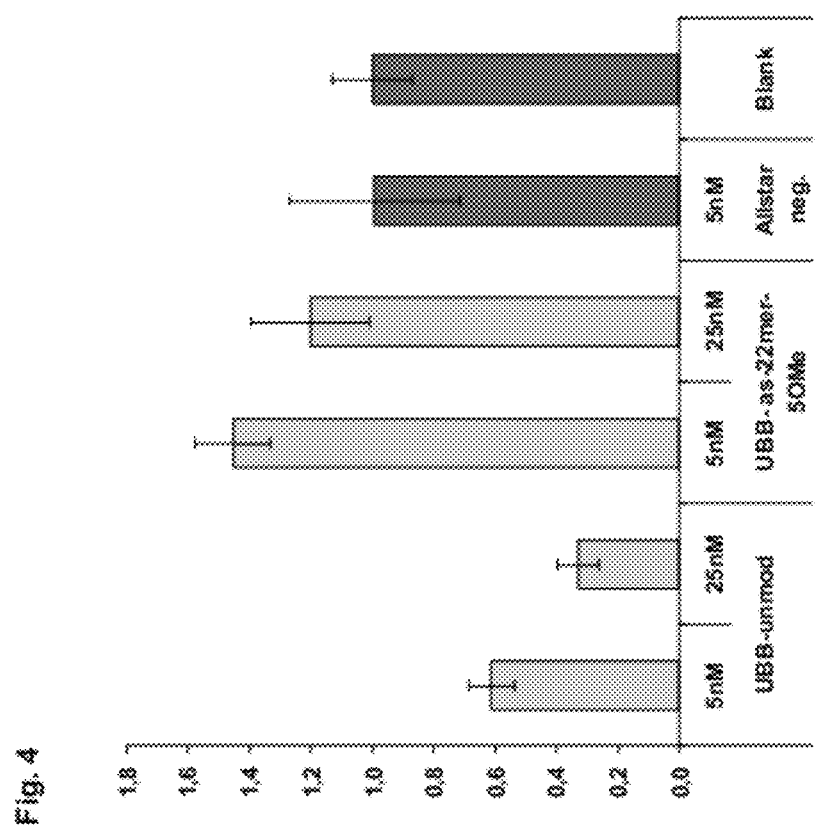

FIG. 4 HeLa S3 cells transfected with Ubiquitin b (Ubb)-specific siRNA: The unmodified duplex is compared with a 5'-OMe-T modified antisense strand (22-mer, 5'-mismatch). The 5'-OMe nucleotide is sequence-independently attached 5' of the complementary region of the antisense strand and does not base-pair. Analysis is performed 48 h after transfection by qRT PCR. Allstar=negative control siRNA (QIAGEN, commercially available product). Blank=no siRNA was transfected. The results show that the 5' OMe blocking is also effective when the modified first nt is not base-paired.

Figure 5:
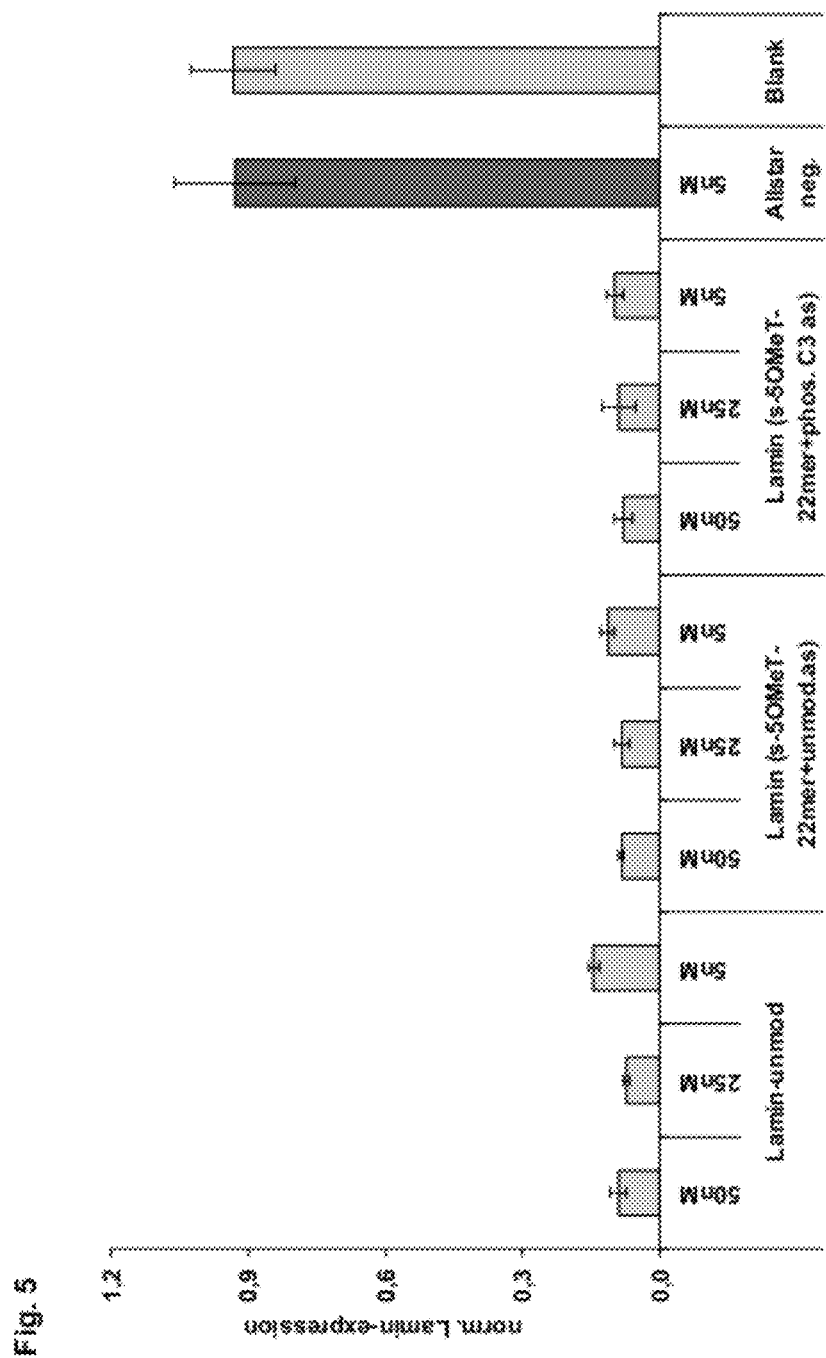

FIG. 5 HeLa S3 cells transfected with Lamin NC specific siRNA: A side by side test ist performed with the following siRNAs:
   the unmodified duplex
   a modified siRNA only having a 5' OMe-T modification
   a fully modified siRNA having a 22-mer sense strand with 5' OMe-T modification and a 5' phosphorylated antisense strand with internal abasic modification (C3-Spacer)
   HeLa cells were transfected with the indicated concentrations of siRNA. 2 days after transfection the cells were lysed, total RNA isolated and the target gene expression was analyzed by qRT PCR. GAPDH mRNA was used for normalization, untransfected cells (blank) were set 1 (100%). Allstar=negative control (QIAGEN, commercially available product). Blank=no siRNA was transfected.

Figure 6:
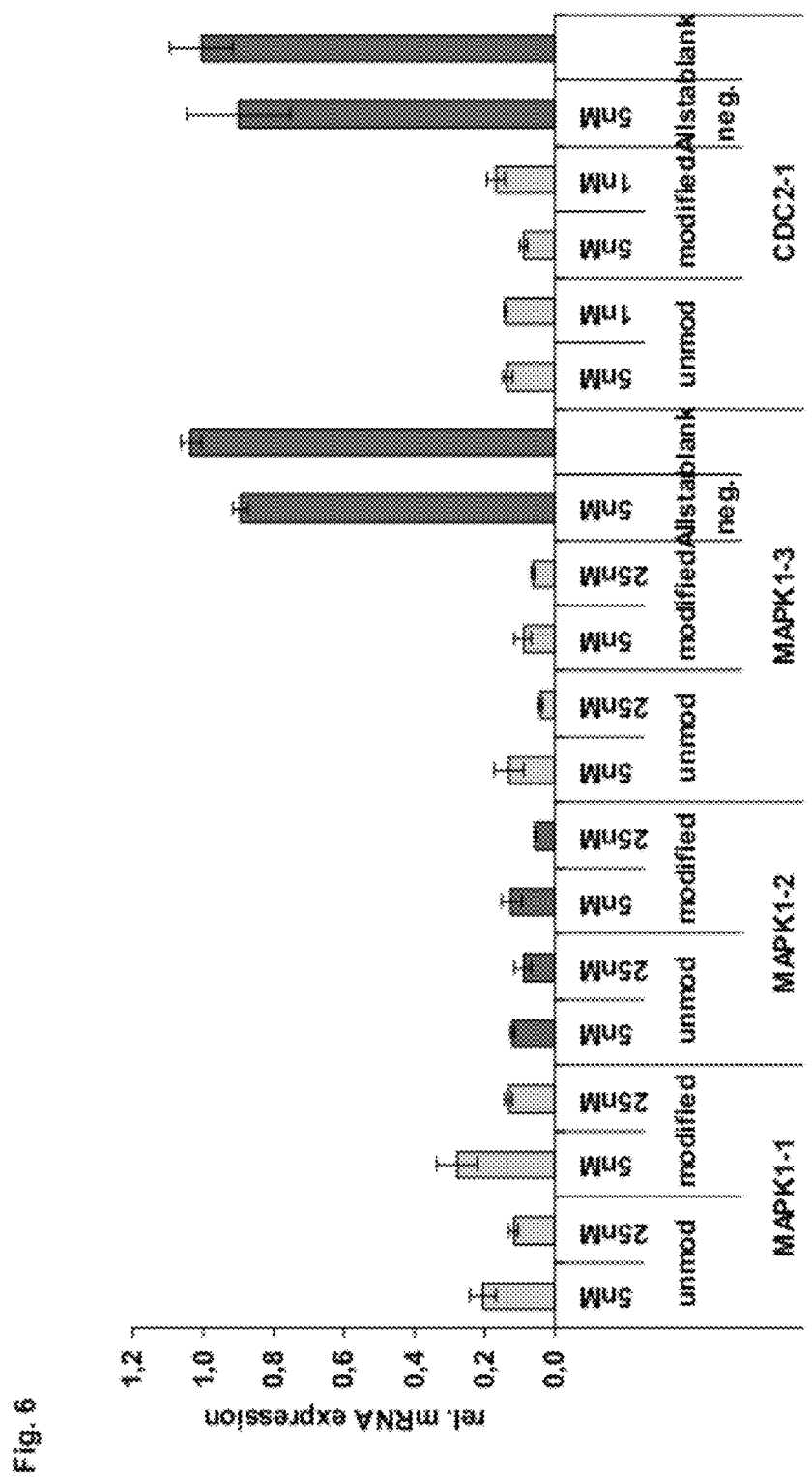

FIG. 6 HeLa S3 cells transfected with MAPK1- or CDC2-specific siRNA: Side-by side test of the unmodified duplex with siRNA containing a 5'-OMe-T modified sense strand and a C3-Spacer modified, 5'-phosphorylated antisense strand. 2 days after transfection the cells were lysed, total RNA isolated and the target gene expression was analyzed by qRT PCR. GAPDH mRNA was used for normalization, untransfected cells (blank) were set 1 (100%). Allstar=negative control (QIAGEN, commercially available product). Blank=no siRNA was transfected.

Figure 7:
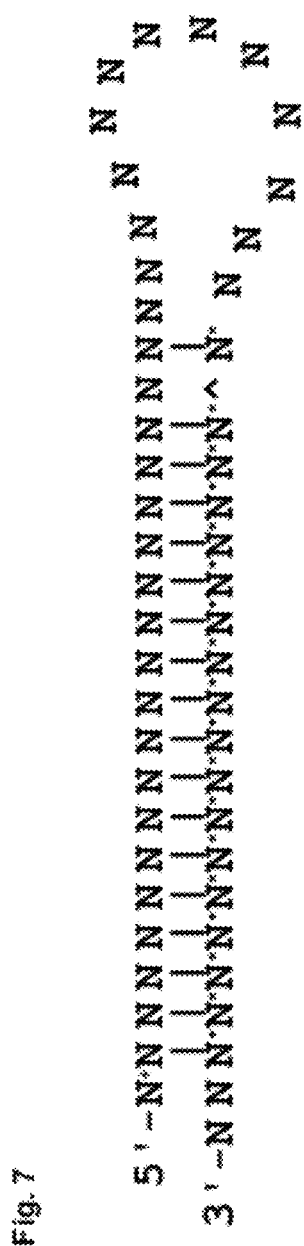

FIG. 7 shows an exemplary structure of a short hairpin siRNA having an abasic modification at position 2 of the antisense strand, an additional 5'-OMe modified nucleotide at the 5' end of the sense strand, and a nucleic acid hairpin structure connecting the 3' end of the sense strand with the 5' end of the antisense strand.

Figure 8:
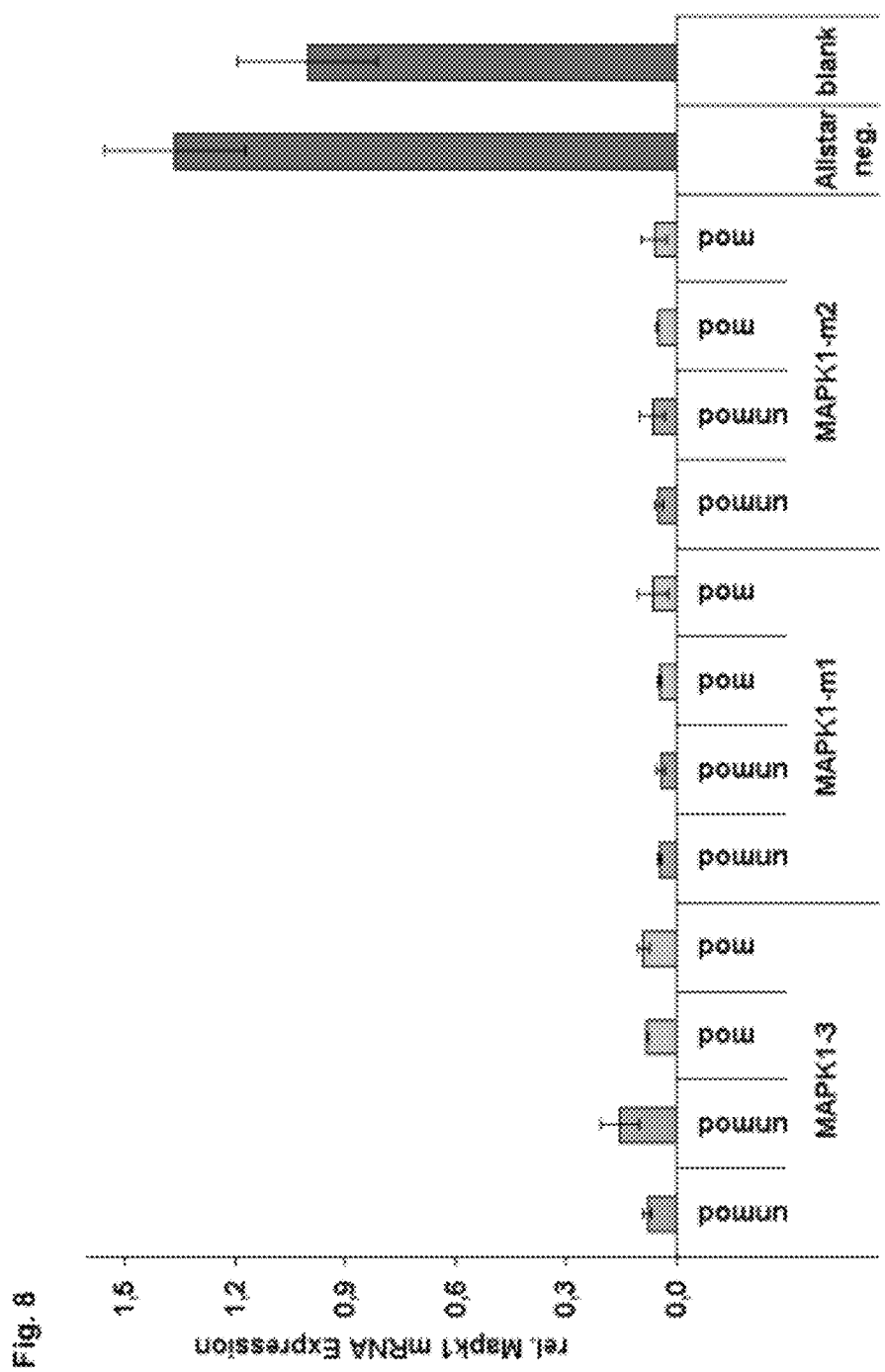

FIG. 8 HeLa S3 cells transfected with three different MAPK1-specific siRNA: Side-by side test of the unmodified duplex with siRNA containing a 5'-OMe-T modified sense strand and a C3-Spacer modified, 5'-phosphorylated antisense strand. 2 days after transfection with 25 nM siRNA the cells were lysed, total RNA isolated and the target gene expression was analyzed by qRT PCR. GAPDH mRNA was used for normalization, untransfected cells (blank) were set 1 (100%). Allstar=AllStars Negative Control siRNA (QIAGEN, commercially available product). Blank=no siRNA was transfected.

Figure 9:
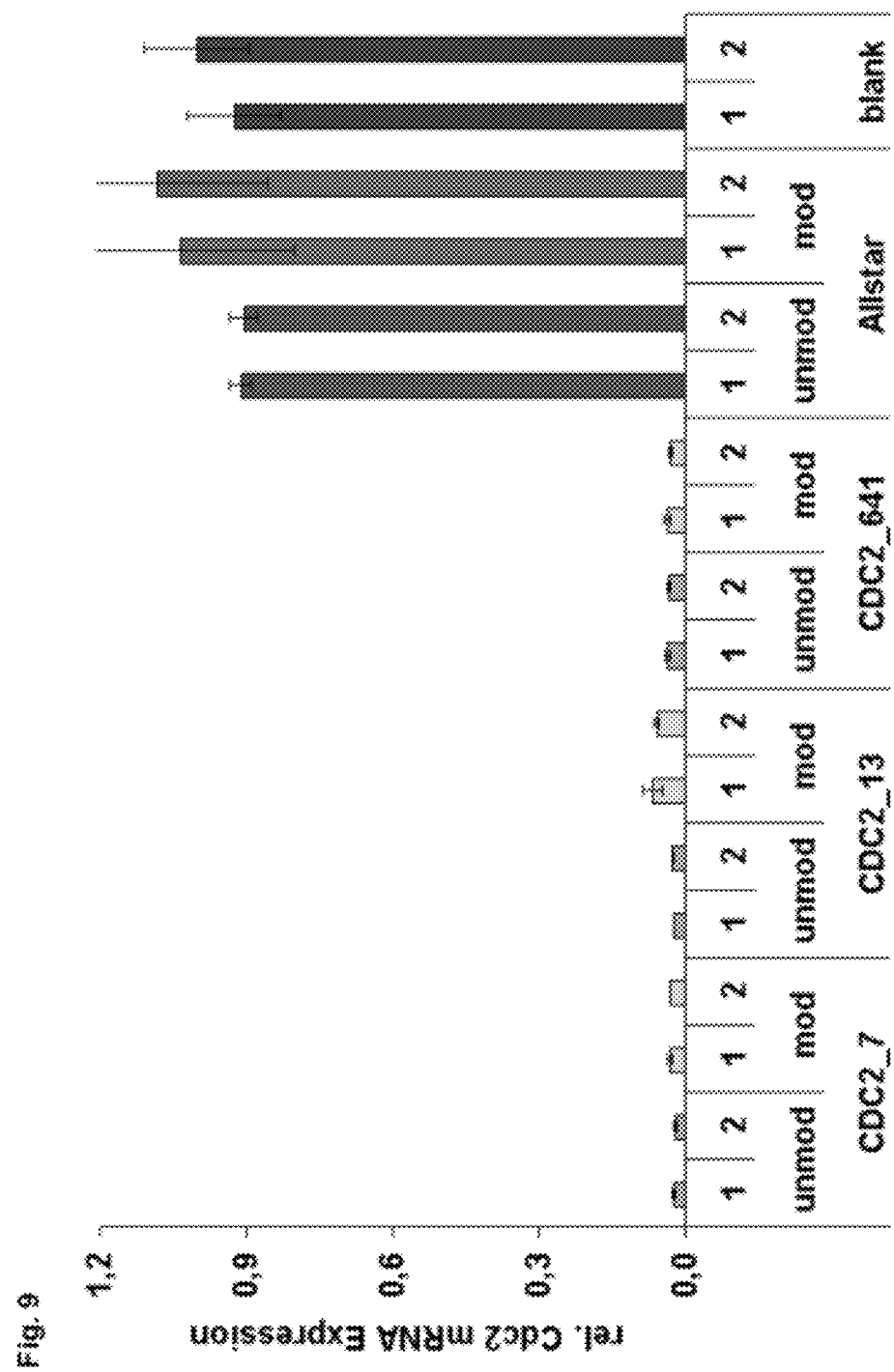

FIG. 9 HeLa S3 cells transfected with three different CDC2-specific siRNA: Side-by side test of the unmodified duplex with siRNA containing a 5'-OMe-T modified sense strand and a C3-Spacer modified, 5'-phosphorylated antisense strand. 2 days after transfection with 25 nM siRNA the cells were lysed, total RNA isolated and the target gene expression was analyzed by qRT PCR. GAPDH mRNA was used for normalization, untransfected cells (blank) were set 1 (100%). Allstar=AllStars Negative Control siRNA (QIAGEN, commercially available product). Blank=no siRNA was transfected.

Figure 10:
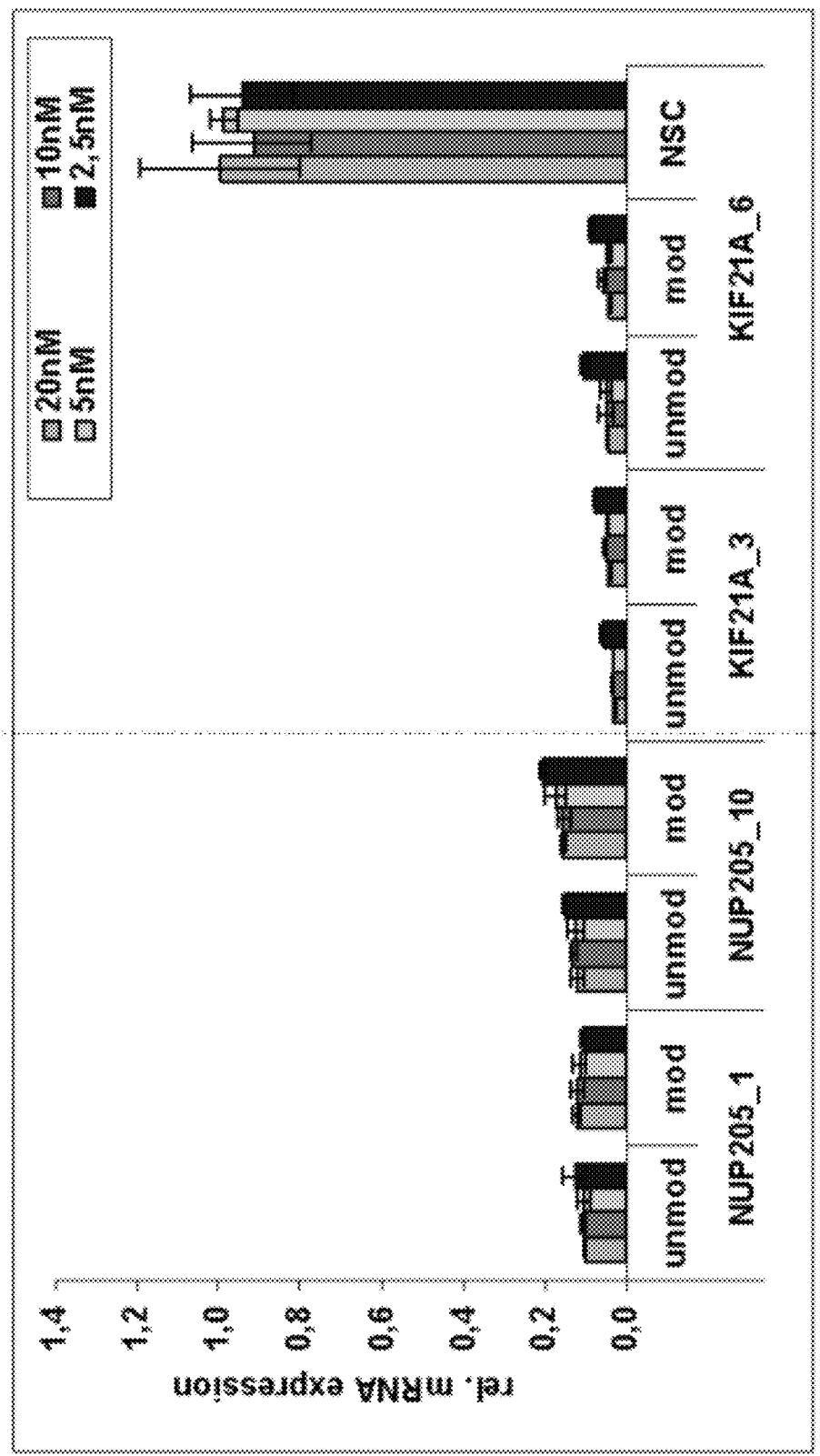

FIG. 10 HeLa S3 cells transfected with Nucleoporin 205kDa- or Kinesin family member 21A-specific siRNA: Side-by side test of the unmodified duplex with siRNA containing a 5'-OMe-T modified sense strand and a C3-Spacer modified, 5'-phosphorylated antisense strand. Between 2.5 and 20 nM siRNA was transfected. 2 days after transfection the cells were lysed, total RNA isolated and the gene expression was analyzed by qRT PCR. GAPDH mRNA was used for normalization, untransfected cells (blank) were set 1 (100%). NSC=AllStars Negative Control siRNA (QIAGEN, commercially available product).

Figure 11:
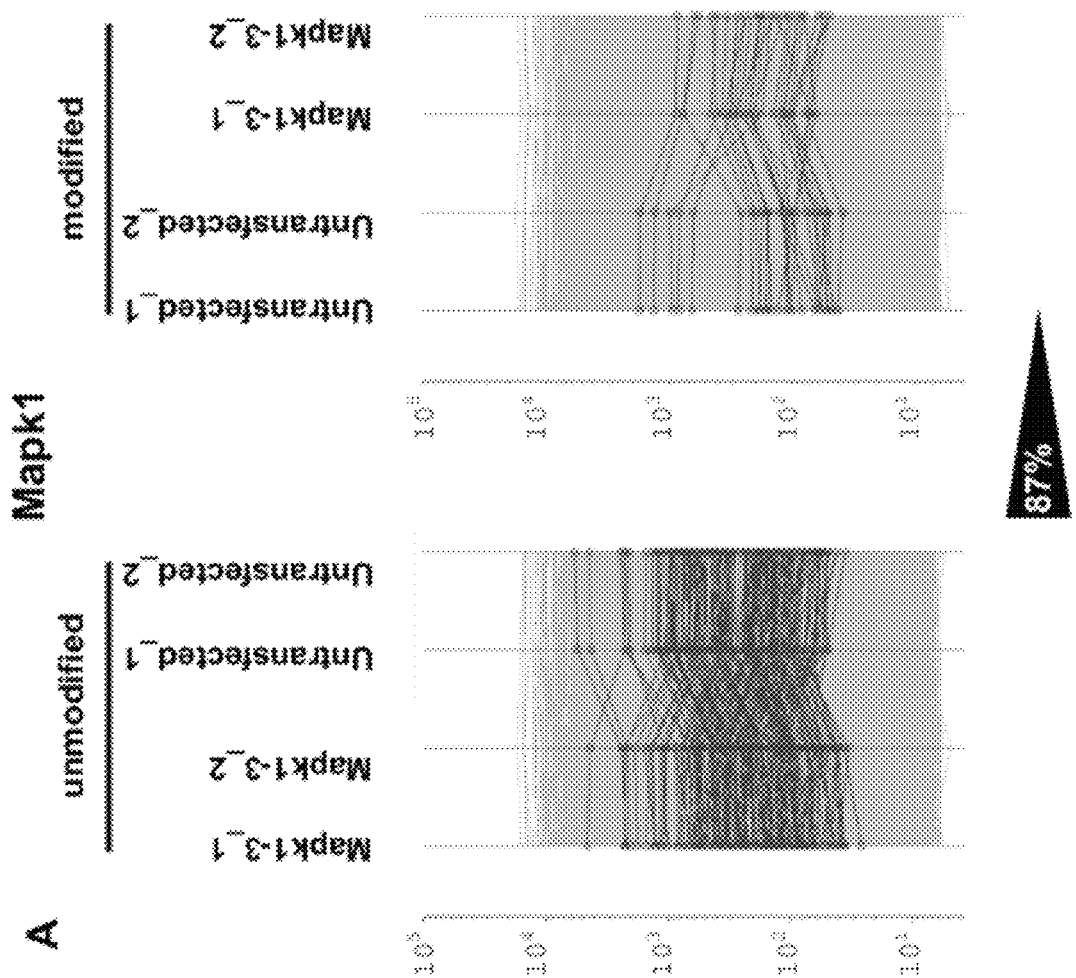
Figure 11:
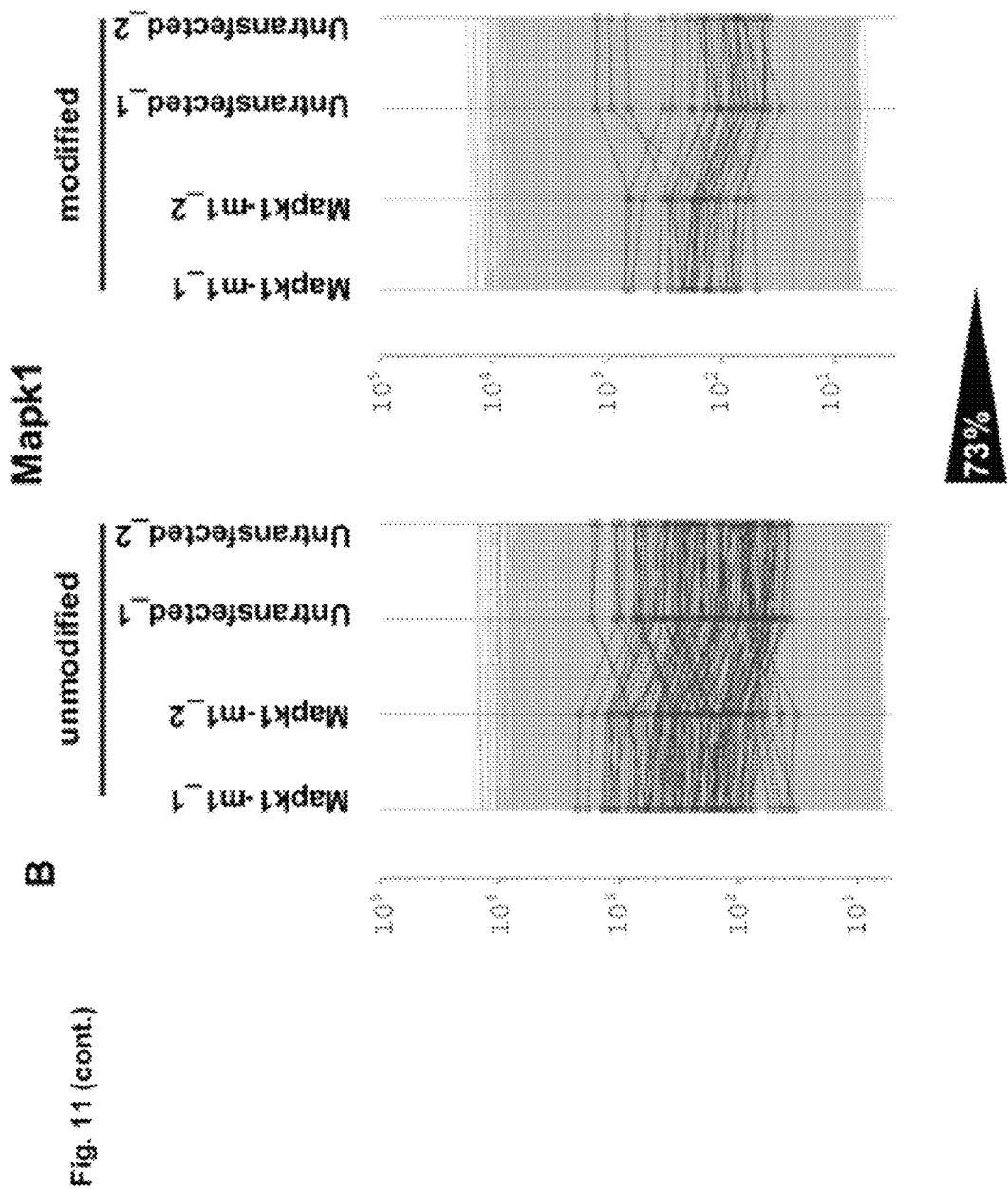
Figure 11:
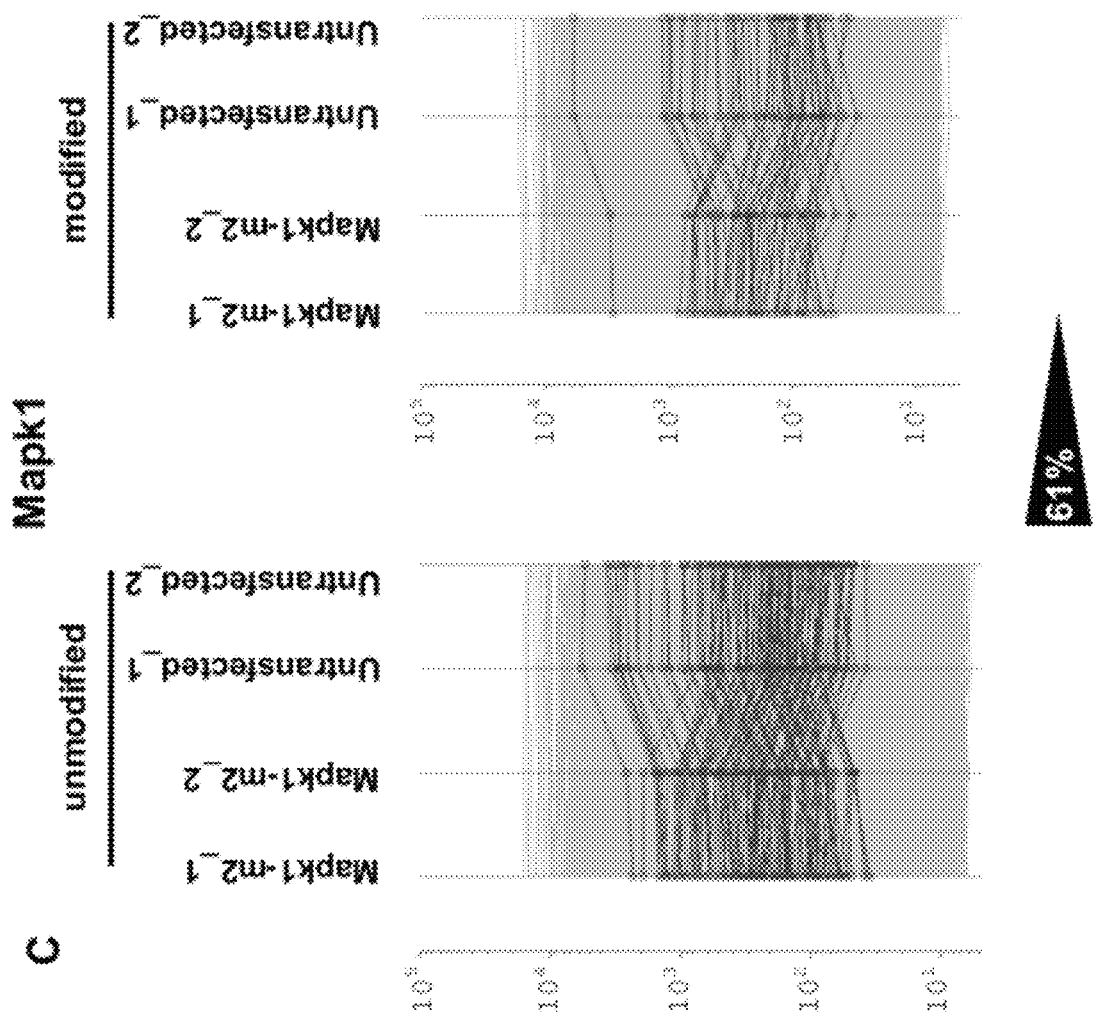

FIG. 11 HeLa S3 cells transfected with three different MAPK1-specific siRNA: Off-target evaluation comparing the unmodified duplex with siRNA containing a 5'-OMe-T modified sense strand and a C3-Spacer modified, 5'-phosphorylated antisense strand. 2 days after transfection with 25 nM siRNA the cells were lysed, total RNA isolated and the genome-wide mRNA expression was analyzed by qRT PCR. The amount of individual mRNAs for the different setups is shown. A, B, C: different MAPK1-specific siRNAs; black lines: amount of mRNA with a change in expression level of more than 2-fold between siRNA-transfected and untransfected cells; gray lines: amount of mRNA with a change in expression level of less than 2-fold between siRNA-transfected and untransfected cells. The indicated percentage represents the reduction in the number of affected mRNAs when using modified siRNA compared to unmodified siRNA.

Figure 12:
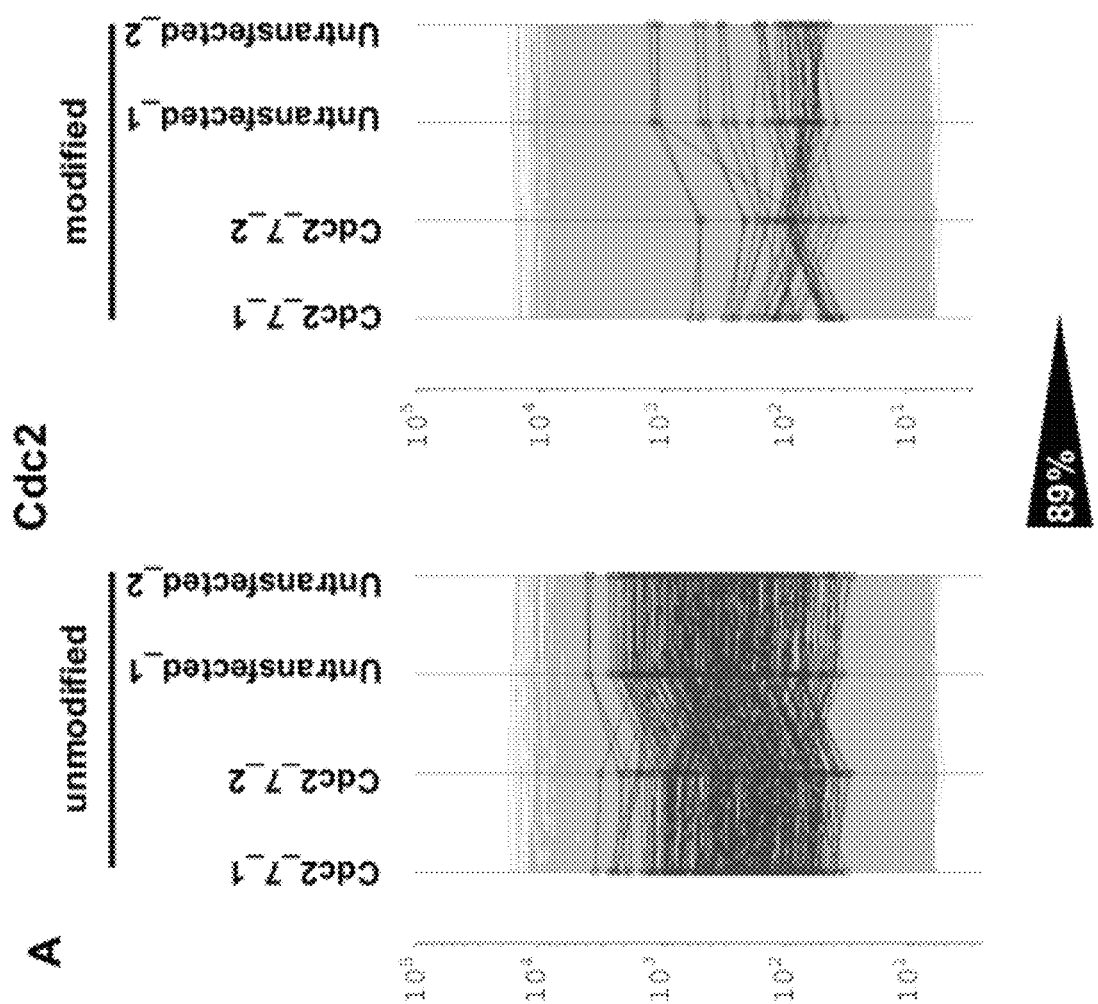
Figure 12:
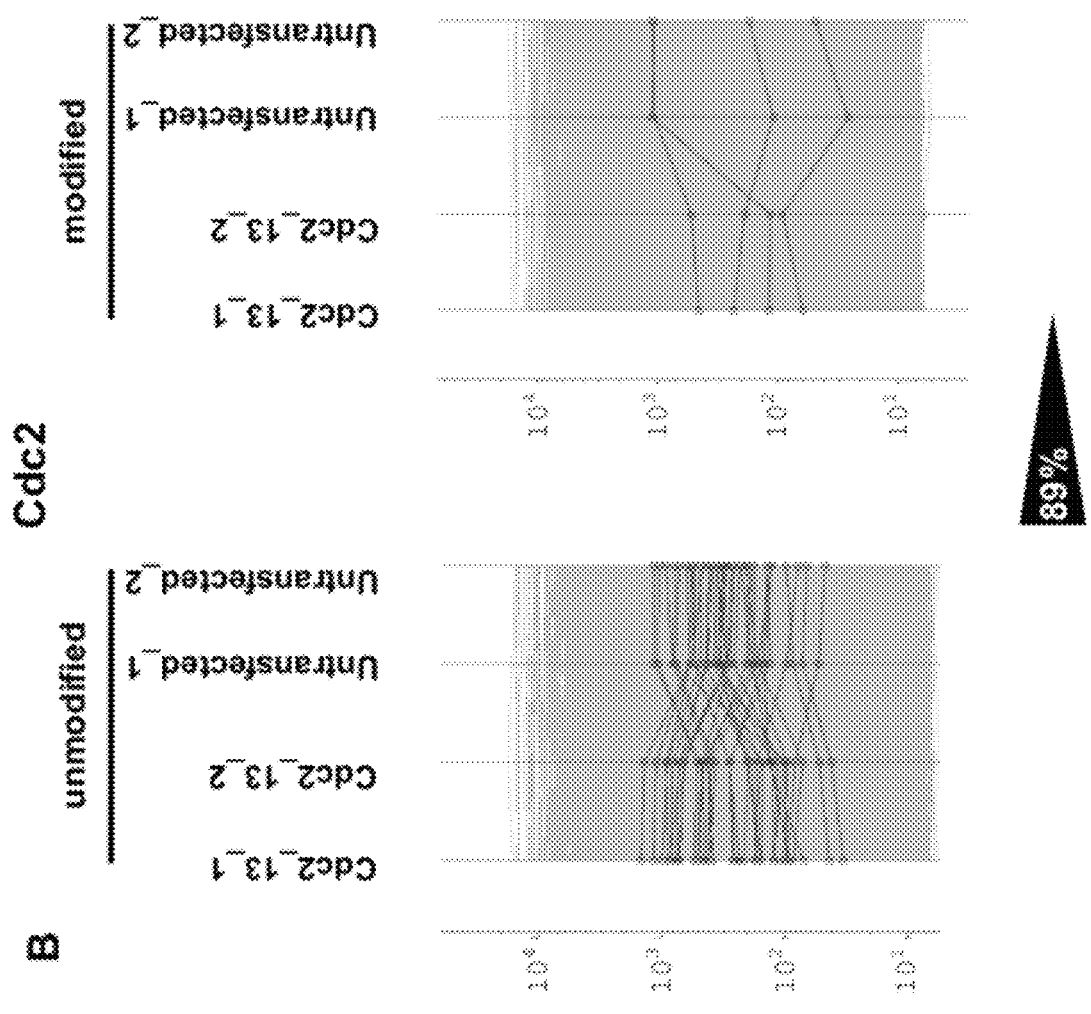
Figure 12:
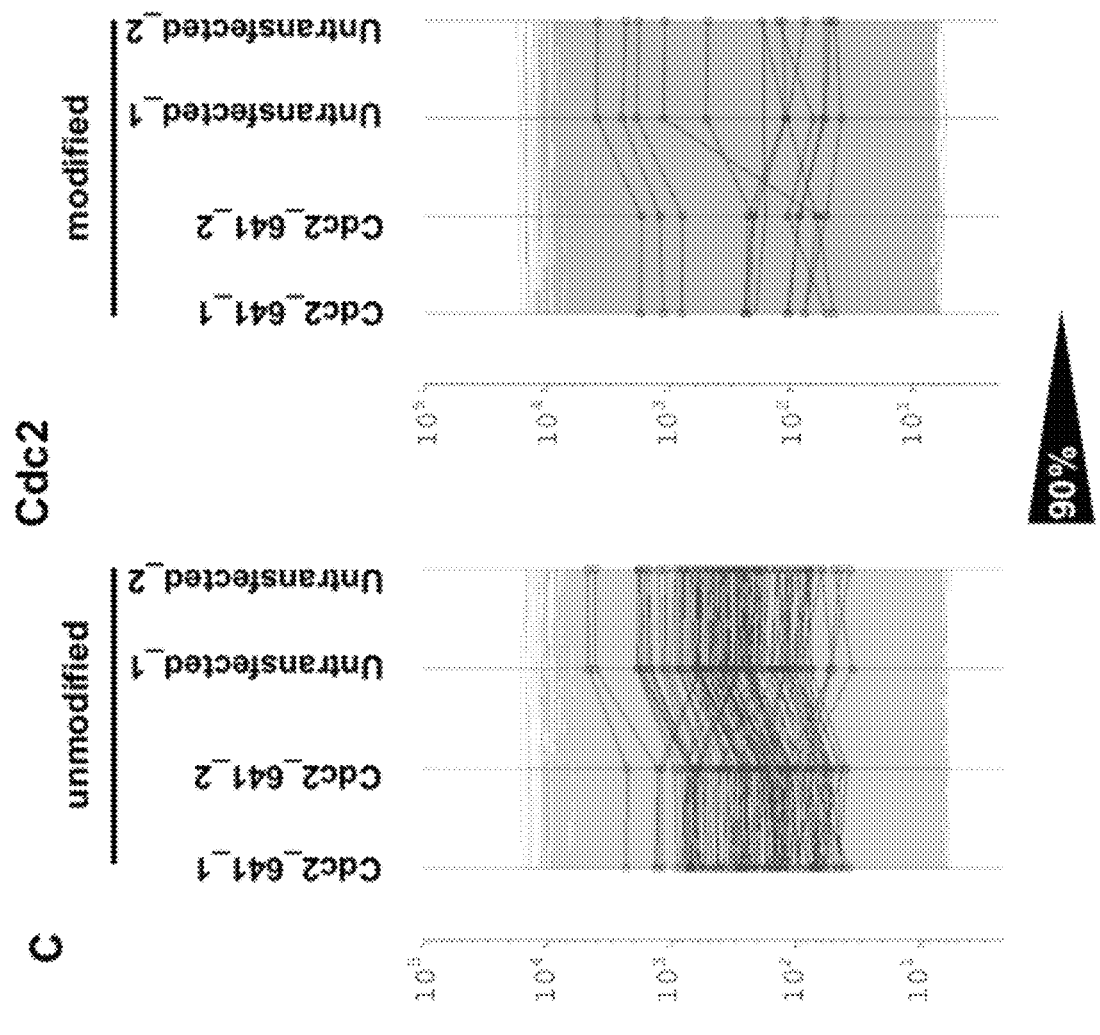

FIG. 12 HeLa S3 cells transfected with three different CDC2-specific siRNA: Off-target evaluation comparing the unmodified duplex with siRNA containing a 5'-OMe-T modified sense strand and a C3-Spacer modified, 5'-phosphorylated antisense strand. 2 days after transfection with 25 nM siRNA the cells were lysed, total RNA isolated and the genome-wide mRNA expression was analyzed by qRT PCR. The amount of individual mRNAs for the different setups is shown. A, B, C: different CDC2-specific siRNAs; black lines: amount of mRNA with a change in expression level of more than 2-fold between siRNA-transfected and untransfected cells; gray lines: amount of mRNA with a change in expression level of less than 2-fold between siRNA-transfected and untransfected cells. The indicated percentage represents the reduction in the number of affected mRNAs when using modified siRNA compared to unmodified siRNA.

Figure 13:
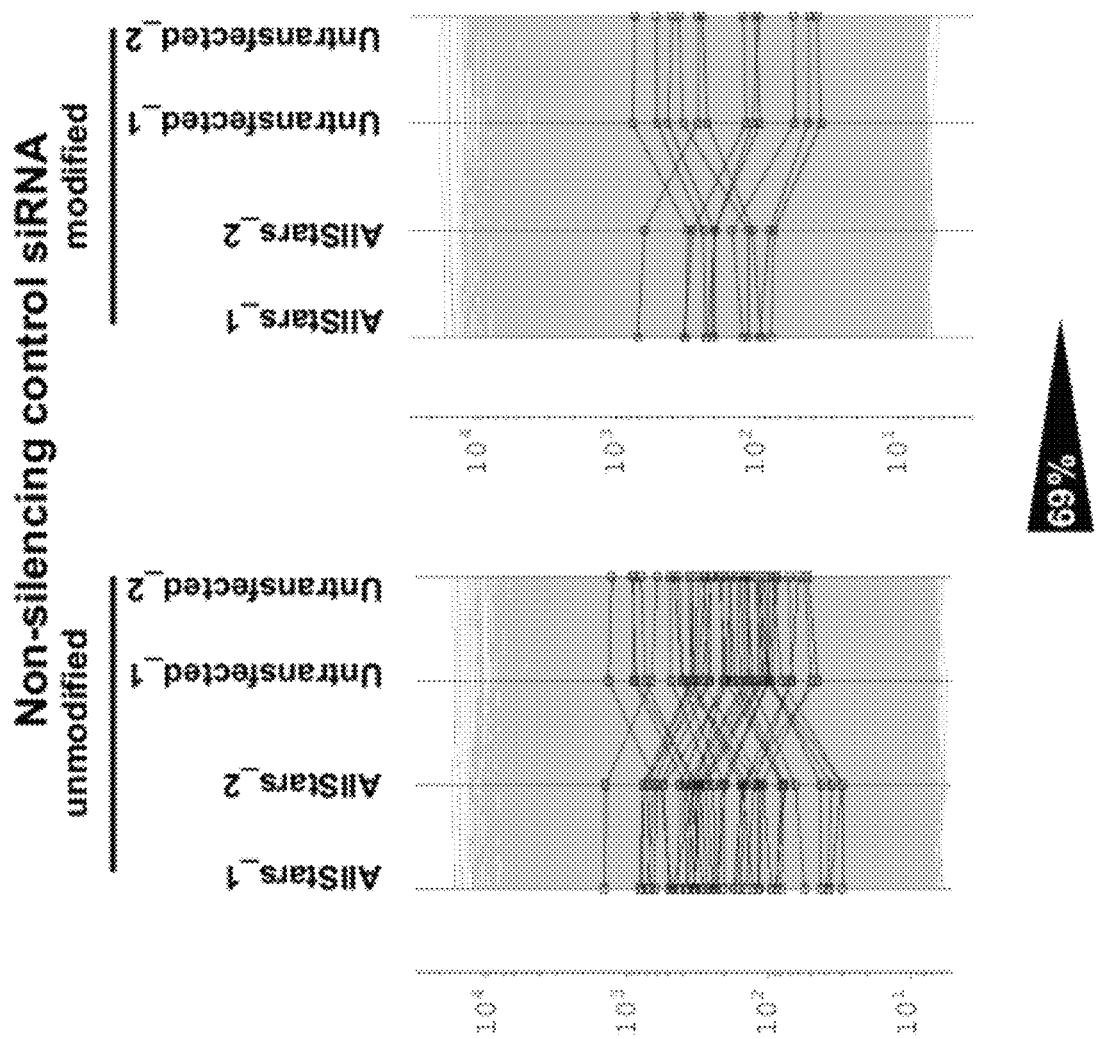

FIG. 13 HeLa S3 cells transfected with non-silencing control siRNA: Off-target evaluation comparing the unmodified duplex with siRNA containing a 5'-OMe-T modified sense strand and a C3-Spacer modified, 5'-phosphorylated antisense strand. 2 days after transfection with 25 nM siRNA the cells were lysed, total RNA isolated and the genome-wide mRNA expression was analyzed by qRT PCR. The amount of individual mRNAs for the different setups is shown. Black lines: amount of mRNA with a change in expression level of more than 2-fold between siRNA-transfected and untransfected cells; gray lines: amount of mRNA with a change in expression level of less than 2-fold between siRNA-transfected and untransfected cells. The indicated percentage represents the reduction in the number of affected mRNAs when using modified siRNA compared to unmodified siRNA.

EXAMPLES

Example 1

Stable Duplex Formation of the Modified siRNA

Four different human target mRNAs have been investigated, lamin A/C, Cdc2, Mapk1 and Ubiquitin B. The siRNA sequences used in this approach were validated. The ability of the individual siRNAs to form stable duplexes was tested after annealing of the different combinations using capillary gel electrophoresis.

The results are shown in FIG. 2. The following siRNAs have been tested:

| lane | siRNA |
| --- | --- |
| A01 | Mapk1-3 unmodified (synthesis 1) |
| A02 | Mapk1-3 unmodified (synthesis 2) |
| A03 | Mapk1-3 modified; as: ribose-spacer at pos. 2 |
| A04 | Mapk1-3 modified; as: C3-spacer at pos. 2 |
| A05 | Mapk1-3 modified; s: 5'-O-methylation |
| A06 | Lamin unmodified (synthesis 1) |
| A07 | Lamin unmodified (synthesis 2) |
| A08 | Lamin modified; as: desoxyribose-spacer at pos. 2 |
| A09 | Lamin modified; as: ribose-spacer at pos. 2 |
| A10 | Lamin modified; as: 5'-phosphorylated, ribose-spacer at pos. 2 |
| A11 | Lamin modified; as: C3-spacer at pos. 2 |
| A12 | Lamin modified; as: 5'-phosphorylated, C3-spacer at pos. 2 |

In case of the modified siRNAs, the modified strand identified in the above table was combined with the corresponding unmodified strand. According to the results from this experiment, all siRNA combinations could form stable siRNA duplexes migrating with the expected molecular size.

Example 2

Similar Knock-Down Efficacy of the Modified siRNA

In transfection experiments, the silencing capability of these modified siRNAs was assessed in comparison to unmodified counterparts. To do so, HeLa S3 cells were transfected with different amounts of all individual siRNA duplexes. According to the known potency of the unmodified siRNA, the final concentrations used in this titration experiment have been adapted. The unmodified and the corresponding modified siRNA always have identical sequences (except for the modification) and were always used in the same amount. Cells were seeded in 24-well plate at a density of 6×10⁴/well. Cells were transfected using 3 μl HiPerFect transfection reagent/well. 48 h after transfection, cells were harvested and total RNA was isolated using RNeasy procedure (QIAGEN, commercially available product). Total RNA was reverse transcribed and the individual target mRNA levels were analyzed using a One-Step RT PCR system with PCR primers specific for the individual mRNA. For normalization of the expression levels, GAPDH mRNA from each RNA sample was amplified in a separate reaction.

The results are shown in FIGS. 3 to 6.

Inhibitory Effect of the 5'-OMe Modification

In a first set of experiments, the inhibitory effect of a 5'-methylation was tested. To this end, the knock-down efficacy of a modified siRNA against Ubiquitin b mRNA having a methylated 5'-OH group at the antisense strand was compared to that of the corresponding unmodified siRNA. As control, non-transfected cells and transfection with AllStars Negative Control siRNA (an siRNA which has no significant homology to any human gene and thus, does not sequence specifically silence any genes; provided by QIAGEN, Hilden, Germany) were used. In a first experiment, the modified siRNA antisense strand was used in a duplex with an unmodified sense strand (FIG. 3) and in a second experiment the modified sense strand was used without any sense strand (FIG. 4). The results demonstrate that essentially no inhibition of the target mRNA occurs when using a modifier siRNA having a 5'-O-methylated antisense strand. However, using the same amount of unmodified siRNA, a significant reduction of the target mRNA amount can be observed. Thus, a 5'-OMe modification of an siRNA strand effectively blocked the inhibiting activity of said strand. This effect was independent of whether the modified nucleotide is base-paired or not. Therefore, a sense strand with a 5'-OMe modification does not cause non-target silencing effects.

No Influence of the Antisense Modifications on the On-Target Effects

To test whether the modifications used for reducing off-target effects have any influence on the on-target effect of the siRNAs, modified siRNAs were compared with the corresponding unmodified siRNAs in target mRNA knock-down experiments. Except for the experiments using Lamin-specific siRNA, the modified siRNAs had a 5'-O-methylation at the sense strand and an abasic modification (C3-spacer) at position 2 and a 5'-phosphorylation at the antisense strand. The following siRNAs were used:

| target gene | siRNA | target sequence |
| --- | --- | --- |
| Ubiquitin b | Ubb | SEQ ID NO: 1 |
| Lamin A/C | Lamin | SEQ ID NO: 2 |
| Mitogen-activated protein kinase 1 | MAPK1-1/MAPK1-m1 | SEQ ID NO: 3 |
| | MAPK1-2/MAPK1-m2 | SEQ ID NO: 4 |
| | MAPK1-3 | SEQ ID NO: 5 |
| CDC2 | CDC2-1 | SEQ ID NO: 6 |
| | CDC2_7 | SEQ ID NO: 7 |
| | CDC2_13 | SEQ ID NO: 8 |
| | CDC2_641 | SEQ ID NO: 9 |
| Nucleoporin 205 kDa | NUP205_1 | SEQ ID NO: 10 |
| | NUP205_10 | SEQ ID NO: 11 |
| Kinesin family member 21A | KIF21A_3 | SEQ ID NO: 12 |
| | KIF21A_6 | SEQ ID NO: 13 |

The different siRNAs which are specific for the same target gene are directed against different parts of the target mRNA to rule out effects which are only associated with a specific siRNA sequence.

In the experiments done, it was shown that for the target sequences tested here, the siRNAs having an abasic modification at position 2 of the 5'-phosphorylated antisense strand and a 5'-OMe-T modification at the sense strand resulted in a target gene silencing which is similar to that of unmodified siRNA (see FIGS. 5, 6, and 8 to 10).

Thus, the abasic modification in the antisense strand and the 5'-OMe modification of the sense strand do not reduce the efficiency of the siRNA towards its target gene. However, these modifications do reduce non-target effects.

Example 3

Reduced Off-Target Effects of the Modified siRNA

To demonstrate that the modifications in the siRNAs result in a reduction of off-target effects, genome-wide expression changes induced by the transfection of modified and unmodified siRNAs were analyzed. All used modified siRNAs had a 5'-O-methylated sense strand and a 5'-phosphorylated antisense strand with an abasic modification (C3-spacer) at position 2. Modified and the corresponding unmodified siRNAs were used at identical conditions (including the amount of the transfected siRNA) and had identical sequences (except for the modifications).

HeLa S3 cells (6'10$^4$ per well of a 24-well plate) were either not transfected or transfected with the different siRNAs in duplicates (and each molecule as unmodified and modified version in parallel) at a concentration of 25 nM using 3 µl HiPerFect transfection reagent/well. As further control, AllStars Negative Control siRNA (QIAGEN, Hilden, Germany) was used. 48 h after transfection, cells were lysed and total RNA was isolated using the RNeasy kit (QIAGEN). The RNA integrity was checked on Agilent BioAnalyzer. The RIN (RNA integrity number) values of all samples were 9 or higher. The knockdown of the target transcripts was analyzed by qRT PCR. The relative expression (after GAPDH-normalization) was determined by using quantified compared to untransfected cells. The target mRNA expression of untransfected cells was set as 100%.

By using qRT-PCR, it was made sure that the knock-down level of the target mRNAs was comparable between the unmodified and the modified version of one particular siRNA sequence. This was important to make sure that potential changes in global gene expression are not related to a different knock-down level of the targets but to difference in unspecific gene regulation.

For measurement of genome-wide expression changes, Affymetrix GeneCHIP Microarrays were used (Human Gene 1.0 ST) representing more than 28,000 well-annotated human genes (Affymetrix, Santa Clara, Calif., USA; order no. 901085). The RNA samples were further processed using Affymetrix Gene Chip WT Double-stranded cDNA synthesis kit (order no. 900813) and the Hybridization, Wash and Stain Kit (order no. 900720) according to the instructions of the handbooks. The samples were run on the Affymetrix Gene Chip System. Data were analyzed using the RMA CEL condenser Algorithm and further processed using Genedata Expressionist. The threshold that was used to filter out noise was n-fold regulation >2. Thus, only mRNAs which amount/expression level differed more than 2-fold between the siRNA-transfected and the untransfected cells were counted as affected by the siRNA.

The results of these experiments show all affected mRNAs, regardless of whether they are the intended target of the transfected siRNA (on-target effect) or not (off-target effect). However, the on-target effects are identical between the modified and unmodified siRNA, as was demonstrated by the results in example 2, above. Therefore, the differences between the experiments using modified and unmodified siRNA exclusively reflect off-target effects.

For all six examples, the number of regulated transcripts was lower when modified siRNAs have been used (see FIGS. 11 to 13). The graphs in FIGS. 11 to 13 show the amount of mRNA for the two siRNA transfected setups and the corresponding untransfected setups. The values for the same mRNA in the different setups are linked by a line. mRNAs which expression level did not change more than 2-fold between the siRNA-transfected and the untransfected cells are shown in gray in the background, while mRNAs which expression level changed more than 2-fold are shown in the front in black. An increased mRNA expression level in the siRNA-transfected cells may result from secondary effects, e.g. a reduced regulation of mRNA expression due to the inhibition of regulator protein expression by the siRNA.

In general, there have been 80% more hits for unmodified siRNA compared to the same siRNA sequence having the chemical modifications mentioned. The individual number of regulated genes is listed in the following table.

| Gene | | MAPK1 | | | CDC2 | | AllStars |
|---|---|---|---|---|---|---|---|
| siRNA | Mapk1-3 | Mapk1-m1 | Mapk1-m2 | Ccd2_7 | Ccd2_13 | Cdc2_641 | control |
| number of regulated genes — standard | 227 | 116 | 149 | 343 | 27 | 118 | 39 |
| modified | 30 | 31 | 58 | 39 | 4 | 12 | 12 |
| Noise reduction (%) | 86.8 | 73.3 | 61.1 | 88.6 | 89.2 | 89.8 | 69.2 |

Thus, the modifications used in the modified siRNA greatly reduce the off-target effects. Even for the AllStars Negative Control siRNA which does not have a target gene in human cells and thus only produces off-target effects, these unwanted effects are significantly reduced by the used modifications (see FIG. 13). Together with all QC data made before the actual chip hybridization, this is a very strong evidence that the reduction of regulated genes reflects a gain in specificity and a decrease in off-target effects for the modified siRNA.

The invention claimed is:

1. An at least partially double stranded modified short interfering nucleic acid (siNA) molecule capable of down-regulating a target gene via RNA interference, comprising a sense strand and a 5' phophorylated antisense strand,
   wherein the antisense strand has sufficient complementarity to the target sequence to mediate RNA interference and wherein said antisense strand contains a single abasic modification at position 2 of the 5' region,
   wherein the abasic modification is derived from a compound selected from the group consisting of:

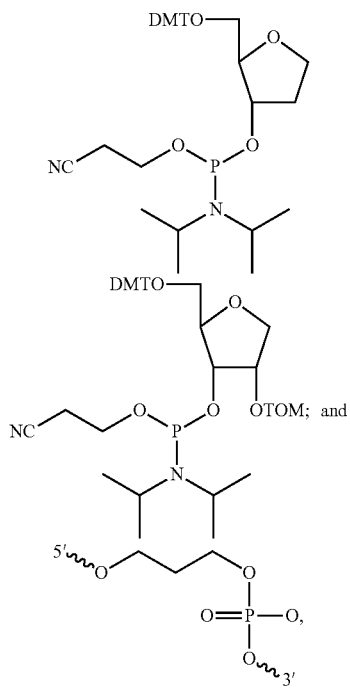

wherein the sense strand contains a single 5' OMe- modification, and
wherein the siNA molecule reduces off target effects by at least 61% relative to an unmodified siNA molecule, but does not reduce on-target effects relative to an unmodified siNA molecule, and wherein the siNA molecule contains no further modifications.

2. The siNA molecule according to claim 1, wherein the antisense strand has at least one of the following characteristics selected from the group consisting of:

a. the first nucleotide of the antisense strand forms part of the double stranded region with the sense strand; and
   b. the antisense strand has a length of 18 to 35 nt.

3. The siNA molecule according to claim 1, wherein the sense strand has at least on of the following characteristics selected from the group consisting of:

a. the 5'OMe- modification forms part of the double stranded region;
   b. the 5'OMe- modification at the 5'end which does not form part of the double stranded region with the antisense strand;
   c. the sense strand comprises a 5 OMe-T, 5' OMe-A, 5' OMe-C, 5' OMe-G or 5' OMe-U at the 5' end; and
   d. the sense strand has a length of 18 to 35 nt.

4. The siNA molecule according to claim 1, wherein the siNA has at least one of the following characteristics selected :from the group consisting of:

a. the siNA forms a duplex which is recognized by the RISC complex;
   b. the double stranded region between the sense and the antisense strand comprises at least 19 nucleotide positions;
   c. the abasic modification is located within the double stranded region formed between the sense and the antisense strand;
   d. the siNA molecule comprises a 3' overhang in the sense strand and/or the antisense strand; and
   e. the siNA is a short hairpin siRNA wherein the 3'end of the sense strand is connected with the 5' end of the antisense strand.

5. The siNA molecule according to claim 1, wherein the siNA molecule has the following characteristic:
   the sense strand and the antisense strand show sufficient complementarity to form a double stranded region spanning at least 17 nucleotide positions and wherein the abasic modification is located within said double-stranded region.

6. A composition comprising the siNA molecule according to claim 1 and one or more buffers.

7. A kit comprising the siNA according to claim 1 and optionally buffers and reagents.

8. The siNA. molecule according to claim 3, wherein the sense strand comprises a 5' OMe-T at the 5' end.

9. The siNA molecule according to claim 4, wherein the siNA has at least one of the following characteristics:

a. the antisense strand comprises a sequence specific 3' overhang; and
   b. the sense strand comprises a sequence unspecific 3' overhang.

* * * * *